United States Patent [19]
Bartley et al.

[11] Patent Number: 6,087,167
[45] Date of Patent: Jul. 11, 2000

[54] ECK RECEPTOR LIGANDS

[75] Inventors: Timothy D. Bartley, Thousand Oaks; William J. Boyle, Moorpark; Gary M. Fox, Newbury Park; Andrew A. Welcher, Glendale; Ella Magal; Richard A. Lindberg, both of Thousand Oaks; Vann P. Parker, Newbury Park, all of Calif.

[73] Assignee: Amgen Inc., Thousand Oaks, Calif.

[21] Appl. No.: 08/959,524

[22] Filed: Oct. 28, 1997

Related U.S. Application Data

[63] Continuation of application No. 08/445,065, May 19, 1995, Pat. No. 5,824,303, which is a continuation-in-part of application No. 08/145,616, Nov. 9, 1993, abandoned, which is a continuation-in-part of application No. 07/977,708, Nov. 13, 1992, abandoned.

[51] Int. Cl.⁷ .............................. C12N 5/00; C12N 5/08; C12N 5/06; A61K 38/00
[52] U.S. Cl. .................... 435/325; 435/366; 435/368; 435/353; 514/12
[58] Field of Search ............... 514/12; 435/325, 435/366, 368, 353

[56] References Cited

FOREIGN PATENT DOCUMENTS

| 0597503 | 5/1994 | European Pat. Off. . |
| WO 9117427 | 11/1991 | WIPO . |
| WO 9207094 | 4/1992 | WIPO . |
| WO 9527060 | 10/1995 | WIPO . |

OTHER PUBLICATIONS

Bartley et al., Nature 368, 558–560 (1994).
Shao, et al., J. Biol. Chem. 270, 5636–5641 (1995).
Pandey et al., Science 268, 567–569 (1995).
Takahashi et al., Oncogene 11, 879–883 (1995).
Magal et al., J. Neurosci. Res. 4 3, 735–744 (1996).
Lindberg, *Tyrosine Phosphorylation & Cell Signalling*, Cold Springs Harbor, New York (May 3–May 7, 1995).

*Primary Examiner*—Ponnathapura Achutamurthy
*Assistant Examiner*—Elizabeth Slobodyansky
*Attorney, Agent, or Firm*—Robert B. Winter; Steven M. Odre; Ron K. Levy

[57] ABSTRACT

Ligands which bind to the eck receptor are disclosed. More particularly, polypeptides which bind specifically to the eck receptor (eck receptor binding proteins or EBPs) and DNA sequences encoding said polypeptides are disclosed. Methods of treatment using eck receptor ligands and soluble eck receptor and disclosed, as are pharmaceutical compositions containing same. A rapid and sensitive method for the detection of receptor binding activity in crude samples is provided.

7 Claims, 14 Drawing Sheets

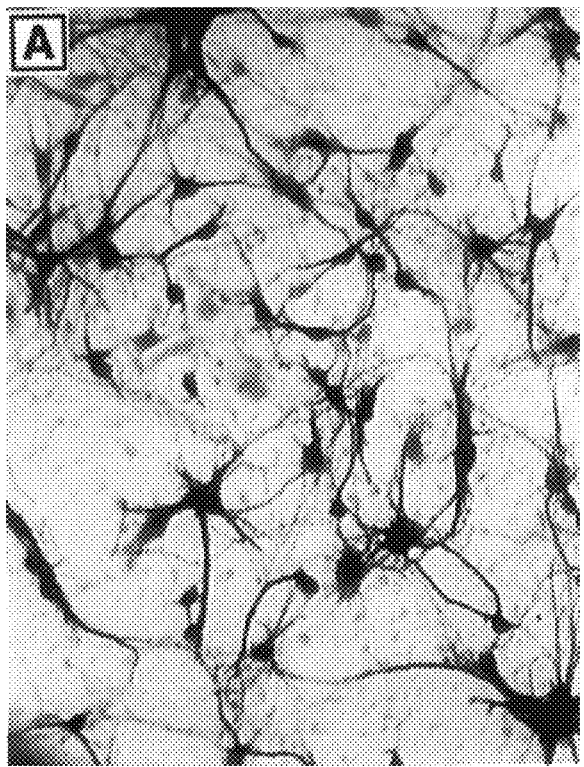
FIG.IIA
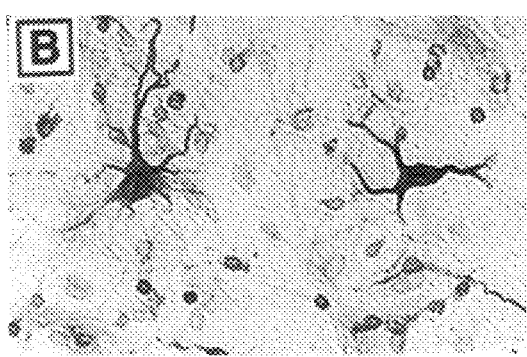
FIG.IIB
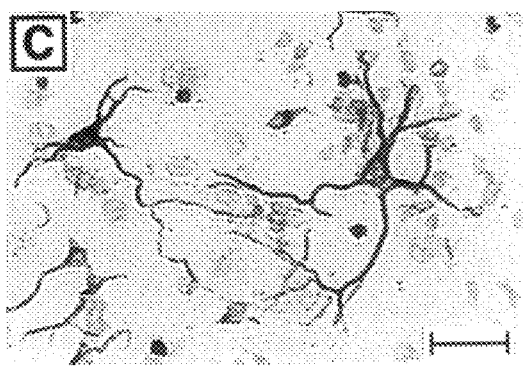
FIG.IIC

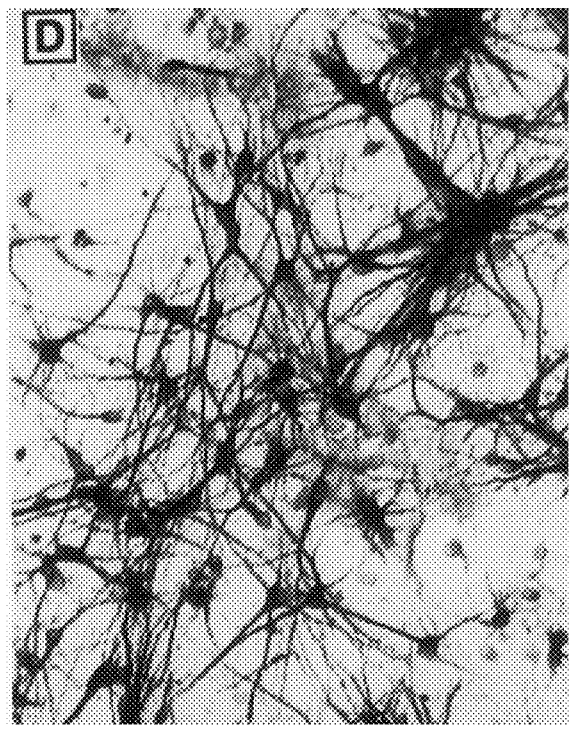
FIG.IID
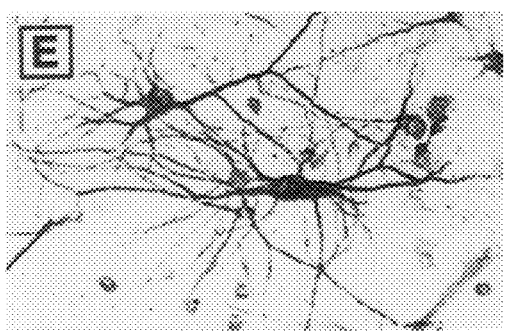
FIG.IIE
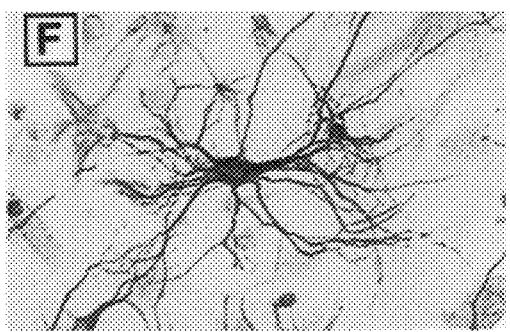
FIG.IIF

6,087,167

ECK RECEPTOR LIGANDS

This application is a continuation of application Ser. No. 08/445,065, filed May 19, 1995, now U.S. Pat. No. 5,824,303, which is a continuation-in-part of Ser. No. 08/145,616, filed Nov. 9, 1993, abandoned, which is a continuation-in-part of Ser. No. 07/977,708, filed Nov. 13, 1992, abandoned, all of which are hereby incorporated by reference.

The invention relates generally to ligands of the eck receptor and, in particular, to polypeptide ligands termed eck receptor binding proteins (EBPs). Also encompassed by the invention are methods of treatment using eck receptor ligands and soluble eck receptor, and pharmaceutical compositions containing same. A rapid and sensitive method for the detection of receptor binding activity in crude samples is described.

BACKGROUND OF THE INVENTION

Peptide growth and differentiation factors elicit responses in target cells by means of specific interactions with receptors at the cell surface. Growth factor receptors are typically membrane glycoproteins with distinct extracellular, transmembrane, and intracellular domains. The structural segregation of the domains corresponds to function (Ullrich et al. *Cell* 61, 203 (1990)); the extracellular domain appears to be responsible for ligand binding and ligand-mediated receptor dimerization (Cunningham et al. *Science* 254, 821 (1991); Lev et al. *J. Biol. Chem.* 267, 10866 (1992)), while the intracellular domain of the receptor, or the intracellular domain of an accessory element (Takeshita et al. *Science* 257, 379 (1992)), is responsible for signal transduction. Much of the specificity of growth factor activity is dictated by the interaction with the binding site on the extracellular domain of the cognate receptor. Chimeric receptors, engineered to contain the extracellular domain of one receptor and the intracellular domain of a second receptor, retain the ligand specificity of the extracellular component (Lehvaslaiho et al. *EMBO J.* 8, 159 (1989)). The downstream signaling pathways activated by such chimeric receptors correspond to those activated by the intracellular component. In many cases soluble forms of receptors, consisting of only the extracellular domains, retain ligand binding activity (Lev et al. i; Duan et al. *J. Biol. Chem.* 266, 413 (1991)). Truncated receptors have been identified in serum (Fernandez-Botran *FASEB J.* 5, 2567 (1991)), cell culture supernatants (Zabrecky et al. *J. Biol. Chem.* 266, 1716 (1991)), and have been produced through recombinant techniques (Lev et al. ibid, Duan et al. ibid).

Recent progress in nucleic acid sequencing and amplification technologies has resulted in the identification of an increasing number of genes which code for previously unidentified growth factor receptors (Wilks *Proc. Natl. Acad. Sci. USA* 36, 1603 (1989); Lai et al. Neuron 6, 691 (1991)). As a result, there is a demand to develop procedures which can define the biological roles of orphan receptors, including techniques which can identify ligands for these receptors (McConnell et al. *Science* 257, 1906 (1992)) Receptor affinity technology is one approach to this problem. This technology may augment existing strategies for the isolation of novel growth factors, since it allows the detection of ligands when biological responses are subtle or undefined.

Recent reports have suggested that the extracellular domains of receptors can be exploited as growth factor-specific affinity reagents. Bailon et al. (*Biotechnology* 5, 1195 (1987)) have shown that the extracellular domain of the IL-2 receptor α subunit can be immobilized on chromatographic media and used for the purification of recombinant IL-2. A genetic fusion of the kit extracellular domain with an alkaline phosphatase enzymatic tag allowed the identification of a cell associated ligand for the receptor (Flanagan et al. *Cell* 63, 185 (1990)). Lupu et al. (*Proc. Natl. Acad. Sci. USA* 89, 2287 (1992)) have reported the affinity purification of an activity which binds to the immobilized extracellular domain of the erbB-2 gene product.

The eck gene, originally identified by cDNA cloning from a human epithelial cell library, encodes a 130 kDa receptor-like protein-tyrosine kinase (p130$^{eck}$) (Lindberg et al. *Mol. Cell. Biol.* 10, 6316 (1990)). Immunohistochemical and mRNA screening of tissues and cell lines suggest that eck expression is highest in cells of epithelial origin. By analogy with genes encoding other receptor-like protein-tyrosine kinases, eck may be a proto-oncogene and therefore may have a role in carcinogenesis. This potential role for eck is more likely given the frequent involvement of epithelial cells in human cancers. Receptor protein kinases are typically activated through interaction with one or more ligands. However, a ligand capable of activating p130$^{eck}$ has not yet been reported. The identification of such a ligand may be important in defining the role of p130$^{eck}$ activation in the development of some human cancers.

It is therefore an object of this invention to identify one or more ligands for p130$^{eck}$. The possible role of p130$^{eck}$ in the transformation of epithelial cells to a cancerous state suggests that identification of the ligand responsible for receptor activation may have therapeutic implications for some epithelial cell-derived malignancies.

SUMMARY OF THE INVENTION

The present invention generally relates to eck receptor ligands. More particularly, polypeptides which bind specifically to the eck receptor, herein referred to as eck receptor binding proteins (EBPs), are disclosed. EBPs were identified and isolated by affinity chromatography using immobilized extracellular eck receptor. EBPs of the present invention may also induce phosphorylation of the receptor upon binding which may trigger changes in target cell physiology, e.g. cell growth and/or differentiation. EBP has an amino acid sequence substantially as shown in SEQ. ID. NO. 1. In a preferred embodiment, EBP has a portion of the amino acid sequence as shown in SEQ. ID. NO. 1. For example, EBP has an amino acid sequence terminating at position 150.

A polypeptide specifically binding the eck receptor, wherein the polypeptide has substantially the same amino acid sequence as shown in SEQ. ID. NO. 1 and has a methionine residue at position −1 is also included. By way of example, the polypeptide is [Met$^{-1}$] EBP$^{1-150}$ or [Met$^{-1}$] EBP$^{1-159}$. Also provided for are DNA sequences encoding same. EBPs may also be analogs which have a portion of the amino acid sequence as shown in SEQ. I.D. NO. 1. Examples of such analogs are EBPs terminating at positions 167, 171 or 180.

The invention also provides for EBP as a product of procaryotic or eucaryotic expression of an exogenous DNA sequence, i.e., eck receptor binding protein is derived from recombinant DNA methods.

A method for detecting receptor binding activity in crude samples by monitoring the binding to an immobilized ligand binding domain of a receptor is also encompassed by the invention.

Pharmaceutical compositions comprising a therapeutically effective amount of an eck receptor ligand are described. Also included is the use of an eck receptor ligand in the treatment of certain types of cancers, particularly those characterized by epithelial cell proliferation. eck receptor ligands may also be used for the treatment of wounds to promote healing, for increasing hematopoiesis, for stimulating the proliferation of hepatocytes and colon crypt cells, and for treating neurological disorders.

The use of therapeutically effective amounts of ligand antagonists or soluble eck receptor for modulating the biological effects of eck receptor ligands is also encompassed by the invention. Such treatments are useful in cancer therapy and in the control of inflammation.

BRIEF DESCRIPTION OF THE FIGURES

FIG. 11. EBP promotes neurite outgrowth in cultured spinal cord neurons. Phase contrast micrographs of MAP2-immunostained 6 day old cultures.

(a) untreated culture; (b) and (c), untreated representative motoneurons (identified morphologically as large neurons with stellate soma and several thick and long processes); (d) culture treated for six days with 500 ng/ml EBP; (e) and (f), representative motoneurons treated for the six days with 500 ng/ml EBP. All photographs are at the same magnification. Scale bar in (c) is 50 $\mu$m.

Figure 12A:
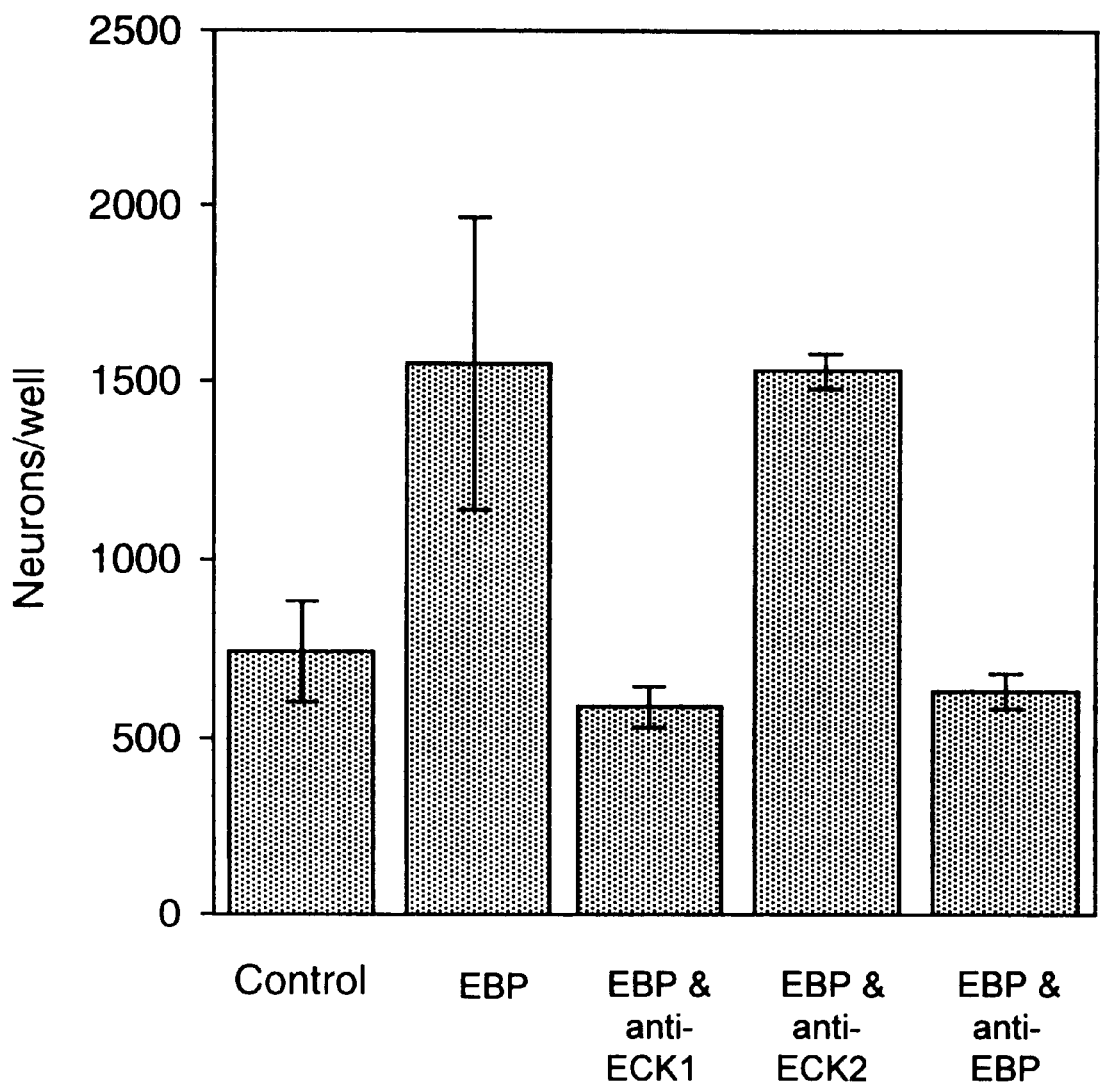
Figure 12B:
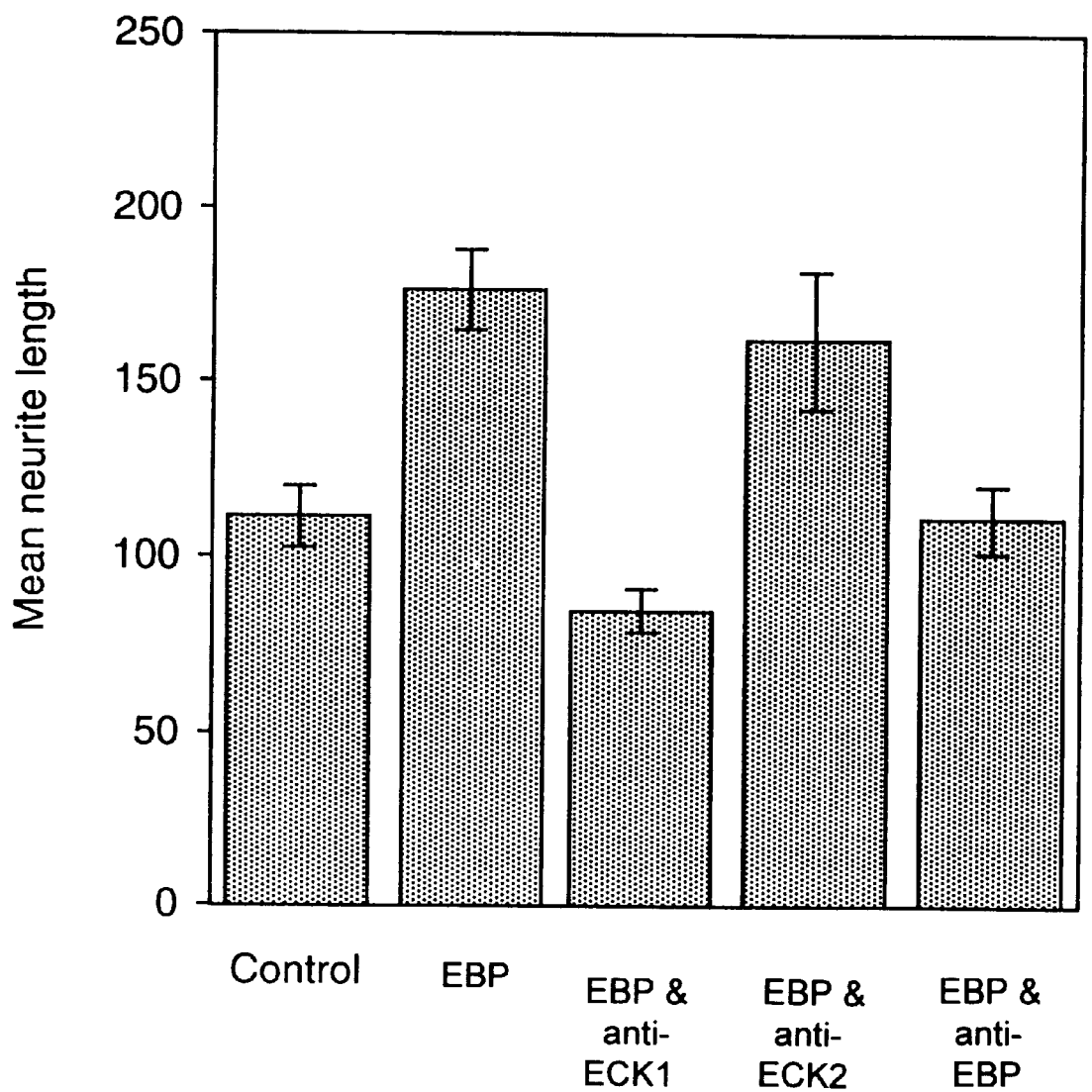

FIG. 12. Involvement of Eck receptor in EBP-mediated motoneuron survival and neurite outgrowth.

(A) Number of motor neurons per well in 3-day old motor neuron enriched cultures either untreated (Control, 753±131) or treated with 250 ng/ml EBP in the absence of antibodies (EBP, 1550±413), in the presence of 15 $\mu$g/ml of an anti-human Eck monoclonal antibody which recognizes the rat Eck extracellular domain (EBP & anti-ECK1, 595±46), in the presence of 20 $\mu$g/ml of an anti-human Eck monoclonal antibody which does not recognize rat Eck (EBP & anti-ECK2, 1532±32), or in the presence of 50 $\mu$g/ml of anti-EBP antibody (EBP & anti-EBP, 629±35). Treatment with EBP significantly enhanced survival over control levels (P<0.005; t test). Addition of anti-EBP and anti-ECK1 antibodies significantly reduced the effects of EBP (P<0.05; t test). Each value is the mean ± SD of 3–7 independent cultures.

(B) Mean neurite lengths ($\mu$m) in motor neuron cultures that underwent treatments similar to those shown in (A): Control (112±9); EBP (177±12); EBP & anti-ECK1 at 6 $\mu$g/ml (85±7); EBP & anti-ECK2 at 8 $\mu$g/ml (162±19); EBP & anti-EBP at 10 $\mu$g/ml (111±10). Each value is the mean ± SE of about 100 neurite length determinations. Survival data from the experiment shown in (B) yielded results similar to those shown in (A).

DETAILED DESCRIPTION OF THE INVENTION

The present invention relates to ligands which bind to the eck receptor, a 130 kDa protein tyrosine kinase identified by Lindberg et al., supra. An eck receptor ligand may activate the receptor by inducing autophosphorylation by the protein-tyrosine kinase catalytic domain. Protein-tyrosine kinases are part of the signal transduction pathway which modulates cell proliferation and differentiation. Therefore, a ligand capable of activating protein-tyrosine kinase activity of the eck receptor will likely be important in modulating the growth and differentiation of cells expressing the receptor. An eck receptor ligand may be a polypeptide, peptide, or non-protein molecule which binds to and/or activates the eck receptor.

The present invention provides for novel polypeptides which specifically bind to the eck receptor. These polypeptides are referred to as eck binding proteins, or EBPs. EBPs have been isolated from the conditioned medium of SK-BR-3 and HCT-8 cell lines by receptor affinity chromatography using the eck receptor extracellular domain (eck-x) as the affinity reagent. Construction of the eck-x gene and expression and purification of eck-x are described in Example 1. The purification of eck binding proteins on immobilized eck-x is described in Example 3A.

Figure 1A:
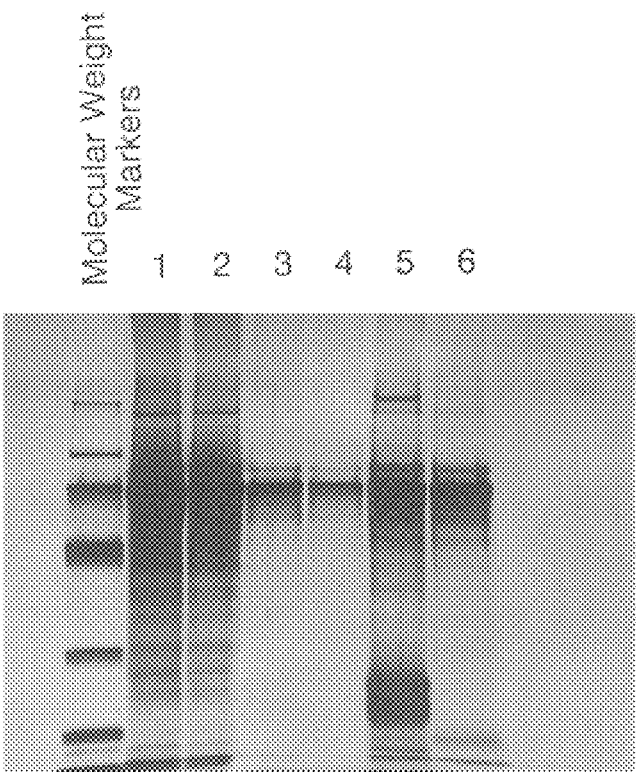
FIG. 1A. SDS-PAGE analysis of immobilized eck-x affinity chromatography. Conditioned medium from HCT-8 cells was concentrated, diafiltered, and loaded onto a 1 ml column of immobilized eck-x (1 mg eck-x per ml of gel). Samples were concentrated in the presence of 0.02% SDS when necessary; equivalent original volumes are shown in parentheses. Lane 1, Column load (20 ml). Lane 2, Unbound fraction (20 ml). Lane 3, PBS wash (50 ml). Lane 4, pH 4.0 elution, fraction 1 (200 ml). Lane 5, pH 4.0 elution, fraction 2 (200 ml). Lane 6, pH 4.0 elution, fraction 3 (200 ml).

EBP derived from the HCT-8 cell line exists in several different molecular weight forms in the range of 21–27 kDa as revealed by SDS-PAGE (FIG. 1A). N-terminal sequencing of EBPs in the 21–27 kDa range revealed a single sequence (Example 3B). After enzymatic removal of carbohydrate chains, a mixture of species in the range of 17–19 kDa was observed, suggesting that the different forms may result from alternative post-translational processing of the protein.

The N-terminal sequence of SK-BR-3 derived EBP was identical to the N-terminal amino acid sequence predicted from the expression of the B61 gene (Holzman et al. *Mol Cell. Biol.* 10, 5830 (1990); PCT Application No. WO 92/07094). The B61 gene was originally identified by differential hybridization as an immediate-early response gene and its expression was induced in cultured human vascular endothelial cells by treatment with tumor necrosis factor-α. Based upon the sequence of the EBP gene, the encoded protein was predicted to have 187 amino acids in its mature form. The isolation and characterization of the EBP-encoded protein has not been previously reported. It was proposed that the EBP protein functions as a cytokine-induced induced marker for inflammation and therefore is useful as a diagnostic reagent for the detection of an impending inflammatory response (PCT Application No. WO 92/07094).

cDNA encoding EBP having the N-terminal sequence determined in Example 3B was cloned and sequenced and, as expected, found to be identical to the B61 gene (Holzman et al. supra). The B61 DNA sequence reported by Holzman et al. is shown in SEQ. ID. NO. 11. The EBP (or EBP gene) was expressed in CHO cells and in *E. coli* as described in Example 4. At least two polypeptides having different molecular weights were expressed by the EBP gene in,CHO cells. C-terminal sequencing of CHO cell EBP revealed only the sequence -lys-arg-leu-ala-ala-COOH which indicated a polypeptide of 150 amino acid residues. This polypeptide is referred to as $EBP^{1-150}$. A polypeptide of 187 amino acids corresponding to the predicted EBP protein, if present at all, represents a very minor product of CHO cell expression. Expression of the EBP gene (lacking the leader sequence) in *E. coli* resulted in a single product on SDS-PAGE having a C-terminal sequence predicted for the full-length protein. This polypeptide which has a methionine residue at the amino terminus is designated [met$^{-1}$] $EBP^{1-187}$ and, with the exception of the N-terminal met, is identical in amino acid sequence to the predicted EBP protein.

CHO cell-derived rEBP has been shown to interact with the eck receptor by the following experiments (see also Example 5): 1) Crosslinking of CHO rEBP to colon carcinoma cells naturally expressing the eck receptor or to CHO cells transfected with the eck gene; 2) equilibrium binding studies of CHO rEBP to eck receptors on colon carcinoma cells; and 3) stimulation of eck receptor phosphorylation on colon carcinoma cells. Induction of receptor phosphorylation by CHO rEBP indicates that the ligand may be able to effect a biological response (e.g., growth or differentiation) in cells displaying the eck receptor.

Figure 1B:
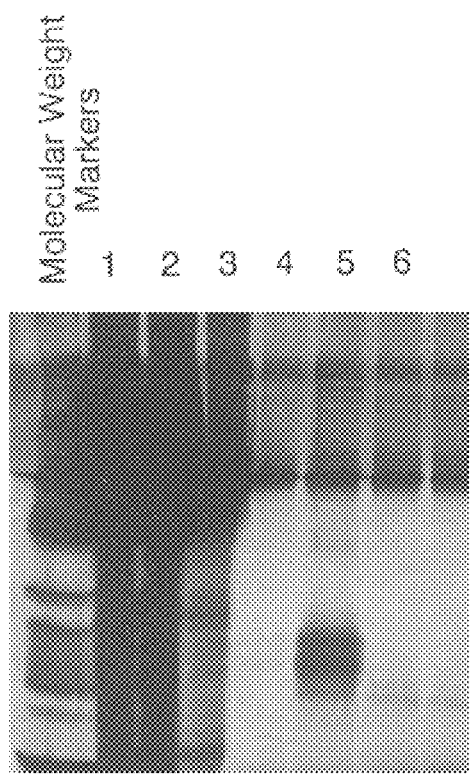
FIG. 1B. SDS-PAGE analysis of immobilized eck-x affinity chromatography. Cell supernatants from CHO cells transfected with EBP gene were treated and analyzed as described in legend to FIG. 1A.
Figure 3:
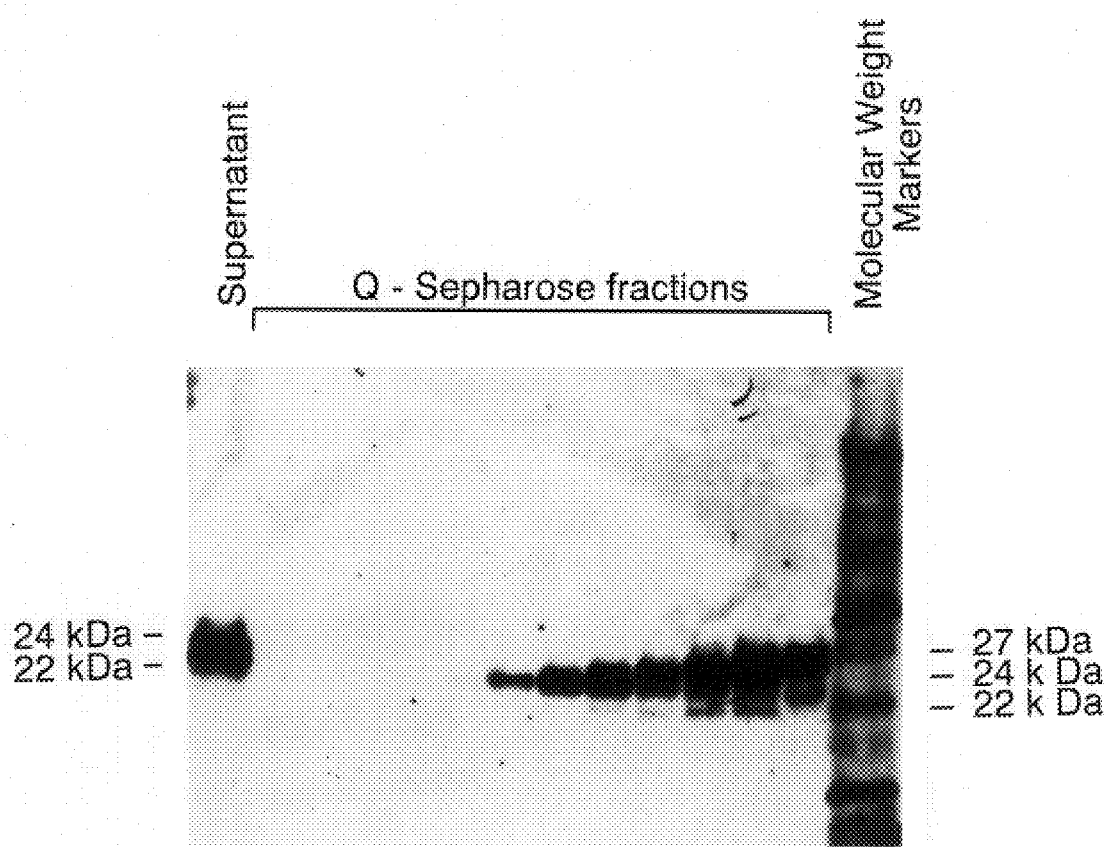
FIG. 3. Q-Sepharose chromatography of EBP from CHO cells transfected with EBP CDNA. Samples were analyzed by SDS-PAGE and probed with anti-EBP antibody.

It is apparent that EBP may be expressed in a number of different molecular weight forms, more than one of which may be biologically active. Various forms of EBP are produced naturally by human cell lines and by EBP gene-transfected host cells as shown in FIGS. 1A and 1B. As shown in FIG. 3, EBP from transfected CHO cells was isolated as two different molecular weight forms of 22 kDa (major) and 24 kDa (minor). Characterization of these different forms revealed two distinct EBPs of 150 and 165 amino acids, designated $EBP^{1-159}$ and $EBP^{1-159}$ Phosphoinositol-phospholipase C treatment of EBP-transfected CHO cell lines releases soluble EBP, strongly suggesting a glycolipid form of EBP. Isolated 27 kDa forms of EBP are susceptible to digestion with phospholipase D further suggesting that these forms are solubilized forms of glycophospholipid-anchored EBP.

The invention provides for EBP having the activity of specifically binding to the eck receptor and having substantially the same amino acid sequence as shown in SEQ. ID. NO. 1. The term "substantially the same amino acid sequence" as used herein refers to deletions or substitutions of amino acids in SEQ. ID. NO. 1 such that the resulting polypeptides specifically ind the eck receptor. As described above, EBP also induces phosphorylation of the eck receptor. However, the present invention encompasses polypeptides which bind the eck receptor and may or may not induce receptor phosphorylation. In a preferred embodiment, EBP has a portion of the amino acid sequence as shown in SEQ. ID. NO. 1. For example, EBP has the amino acid sequence as shown in SEQ ID. NO. 1 terminating at position 150 or has substantially the same amino acid sequence as shown in SEQ. ID. NO. 1 Preferably, EBP is $EBP^{1-150}$, that is, it has the amino acid sequence from positions +1 to 150 as shown in SEQ. ID. NO. 1.

An EBP which has substantially the same amino acid sequence as shown in SEQ. ID. NO. 1 and has a methionine residue at position −1 is also included. [Met$^{-1}$] $EBP^{1-150}$ and [Met$^{-1}$] $EBP^{1-159}$ are examples. Also provided for are DNA sequence encoding same. A truncated DNA sequence encoding amino acid residues +1 to 150 as shown in SEQ. ID. NO. 1 was constructed and expressed in *E. coli*. The resulting protein, [met$^{-1}$] $EBP^{1-150}$, binds to the eck receptor and induces receptor phosphorylation (Example 6).

Also encompassed by the invention are fragments and analogs of the polypeptide encoded by the amino acid sequence shown in SEQ. ID. NO. 1 wherein said fragments and analogs bind to the eck receptor, and DNA sequences encoding said fragments and analogs. Included are fragments having deletions from the N-terminal or C-terminal ends of the polypeptide as shown in SEQ. ID. NO. 1 and deletions from internal regions. Examples of EBP fragments include $EBP^{1-167}$, $EBP^{1-171}$ and $EBP^{1-180}$ described in Example 5. Analogs include amino acid substitutions at one or more sites in the polypeptide. Fragments and analogs of the invention are readily constructed using recombinant DNA techniques which are known to those skilled in the art. The biological activity of the resulting fragments and analogs is readily tested by binding to eck soluble receptor or to eck receptors on cell surfaces and by inducing phosphorylation of the eck receptor.

The invention also includes EBP characterized by being the product of procaryotic or eucaryotic expression of an exogenous DNA sequence, i.e., EBP is recombinant EBP. Exogenous DNA sequences may be cDNA, genomic or synthetic DNA sequences. EBP may be expressed in bacterial, yeast, plant, insect or mammalian cells in culture or in transgenic animals. DNA vectors suitable for the expression of EBP in a variety of host cells are known to one skilled in the art. Examples of such vectors are pDSRα2 for the expression of EBP gene in CHO D- cells and pCFM1156 for the expression of EBP gene in E. coli.

EBP expression in E. coli results in the formation of insoluble inclusion bodies. Recovery of biologically active EBP requires solubilization of EBP aggregates followed by refolding of the solubilized protein. Example 4C describes a refolding procedure for E. coli derived EBP which yields EBP active in eck-x binding and eck phophorylation. EBP refolding procedures may be modified to increase the activity of the renatured protein and to increase the yield of active EBP. Such modifications include changing the denaturant used to solubilize the inclusion body (e.g. using guanidinium chloride vs. urea), the oxidizing agent (which may include oxidation reduction pairs such as oxidized and reduced glutathione), or the dilution protocol from the denaturant (e.g. EBP may be diluted at a different protein concentration into a detergent containing buffer at a modified pH).

Also provided by the invention is a method for detecting a ligand present in crude samples, e.g., conditioned medium, which is capable of binding a receptor. The method comprises the steps of:

a) immobilizing a purified ligand binding domain of the receptor;

b) contacting the immobilized receptor with conditioned medium containing the ligand; and c) monitoring the binding of the ligand to the immobilized receptor by a surface plasmon resonance detection system.

As described in Example 2, this method provides a rapid and sensitive screening for eck receptor binding activity in cell supernatants. The results of this screening are shown in Table 1. Although the method is used to detect eck binding activity, it may be generally applied to any receptor-ligand interaction. Any ligand binding domain of a receptor may be immobilized for the isolation of receptor binding proteins. In a preferred embodiment, the ligand binding domain is the extracellular domain or a fragment or analog thereof which is competent for binding. In addition to screening cell supernatants, the method may also be used to screen mixtures of random sequence peptides for receptor binding.

The invention provides, for the first time, a method of modulating the endogenous enzymatic activity of an eck receptor. Said method comprises administering to a mammal an effective amount of a ligand to the eck receptor to modulate the enzymatic activity of said receptor. eck receptor enzymatic activity regulates cellular functions comprising differentiation, proliferation and metabolism. In a preferred embodiment, EBP, or a fragment or analog thereof, is the ligand. However, other ligands may also be used in modulating eck receptor activity, for example, polypeptides not related to EBP, or peptides and non-protein organic molecules.

Also encompassed by the invention is a method for identifying compounds that modulate the activity of an eck receptor. Said method comprises the steps of:

a) exposing cells exhibiting the receptor to known ligands for a time sufficient to allow formation of receptor-ligand complexes and induce signal transduction;

b) determining the extent of activity within the cells; and c) comparing the measured activity to the activity in cells not exposed to the ligand. Eck receptor activity may be detected by changes in target cell proliferation, differentiation or metabolism. A description of methods relating to the modulation of eck receptor activity on hematopoietic progenitor cells, colon crypt cells and hepatocytes appears in Example 9.

The invention also encompasses an isolated eck receptor-ligand complex which results from the interaction of the eck receptor with a ligand such as EBP. The interaction may result in activation of the receptor and transduction of a signal which modulates the physiological state of the receptor-bearing cells. Preferably, the ligand acts as a growth factor to stimulate the proliferation of target cells. Alternatively, ligand binding may not activate the eck receptor. In this instance, the ligand may act as an antagonist for other molecules which activate the receptor and induce in signal transduction.

The eck receptor is expressed primarily in tissues containing significant amounts of epithelial cells (e.g. lung and intestine) and in cell lines derived from epithelial cells (Lindberg et al., suora). A ligand of the eck receptor may stimulate either the growth or differentiation of cells expressing the receptor. A ligand which induces differentiation of cells bearing the eck receptor may be useful in the treatment of certain types of cancers, particularly those resulting from proliferation of epithelial cells. An eck receptor ligand may be used alone or in combination with standard chemotherapy or radiation therapy for cancer treatment.

EBP interaction with the eck receptor may be involved in the development of a cancerous state through stimulation of cell growth or may promote metastasis by stimulating cell mobility and adhesion. Several strategies are available for modulating the biological effects of EBP. Fragments or analogs of EBP which bind to but do not activate the eck receptor are useful as EBP antagonists. Administration of an EBP antagonist having affinity for the eck receptor will block receptor binding and activation by circulating EBP. Administration of soluble eck receptor may also be used to counteract the biological effects of EBP. Soluble eck receptor will compete with cell surface receptors for binding to EBP and thereby reduce the extent of eck receptor activation by EBP. Soluble eck receptors suitable for therapeutic use include the receptor protein described in Example 1 as well as fragments and analogs thereof which bind EBP. In addition, monoclonal antibodies directed either to EBP or to the eck receptor may be useful in blocking the interactions of EBP with eck receptors on cell surfaces.

Expression of the EBP gene in endothelial cells has been shown to be stimulated by TNF-α and IL-1β, two proinflammatory cytokines which activate various functions in endothelial cells as part of the inflammatory response (Holzman et al. supra). A treatment comprising the administration of soluble eck receptor to reduce levels of EBP that are increased during the inflammatory response may be useful in controlling inflammation.

A method for the treatment of a wound in a mammal comprising administering a therapeutically effective amount of an eck receptor ligand is provided. As shown in Example 9A, EBP promoted an increase in tissue wet weight, total protein, total DNA, and total glycosaminoglycan in the rat wound chamber assay. Since EBP is expressed early in the inflammatory response, it could play a role in the recruitment of epithelial cells to the site of an injury.

A method for increasing hematopoiesis in a mammal comprising administering a therapeutically effective amount of an eck receptor ligand is also provided. As shown in Example 9B, EBP in combination with interleukin-3 (IL-3) shows a significant enhancement of CFU-Cs in mouse bone marrow cultures. EBP would be useful in restoring hematopoiesis when myelosuppression has occurred, either as a result of a disease or after exposure to myelosuppressive agents, such as chemotherapeutic drugs or agents. In a preferred embodiment, a therapeutically effective amount of EBP is used in combination with a therapeutically effective amount of IL-3 for increasing hematopoiesis.

Also included is a method for stimulating the proliferation of colon cells in a mammal comprising administering a therapeutically effective amount of an eck receptor ligand. As shown in Example 9C, EBP stimulates cell proliferation in a colon crypt assay. An eck receptor ligand such as EBP would be useful in alleviating gut toxicity following chemotherapy.

A method for semulating proliferation of hepatocytes comprising administering a therapeutically effective amount of an eck receptor ligand is provided. Example 9D shows stimulation of hepatocytes by EBP. This stimulation is comparable to that seen in the same assay with acidic fibroblast growth factor (aFGF), a known hepatocyte growth factor. Treatment with an eck receptor ligand is useful for repairing liver damage resulting from disease or injury.

As shown in Example 10, EBP promotes neural cell survival in five different rat cell culture systems: embryonic day (E)16 midbrain, E20 mesencephalon, E20 hippocampus, E15 spinal cord and postnatal day (P)5 locus coeroleus. These culture systems are used to study specific neuron types: midbrain and mesenecephalon cultures contain dopamingeric, tyrosine hydroxylase (TH)-positive neurons; hippocampus cultures contain pyramidal neurons; spinal cord cultures contain motor neurons; and locus coeroleus cultures contain noradrenergic, TH-positive neurons. The most pronounced effect of EBP was on survival of motor neurons in spinal cord cultures. Further studies of EBP action on E15 spinal cord cultures revealed that EBP acted through the eck receptor to promote both motor neuron survival and dendrite outgrowth in a dose-dependent manner. EBP activity on a variety of neurons suggests it may be important in modulating the growth and/or differentiation of cell types in the nervous system.

In vitro cultures of cells taken from specific areas of the brain form the basis for in vivo models of certain neurological disorders. The relationship between the culture systems used herein, in vivo models and neurological disorders is described below.

Systemic administration of the neurotoxin MPTP (1-methyl-4-phenyl-1,2,3,6-tetrahyropyridine) destroys nigrostriatal dopamingeric neurons (Heikkla et al., Science 224, 1451–1453 (1984), Langston et al., Brain Res. 292, 390–394 (1984), Davis et al., Psychiatr. Res. 1, 249–254 (1979)) and induces a Parkinsonian syndrome in monkeys and humans. Thus MPTP-injected rats provide one model for studying effects of various factors in Parkinson's related disorders. Another model for Parkinson's is 6-hydroxydopamine-induced lesions of the nigrostriatal dopamine system (Bjorklund et al., Trends Neurosci. 10, 509 (1987)). Both MPTP and 6-hydroxydopamine-induced destruction of dopamingeric neurons may be reversed either by administration of purified neurotrophic factors (e.g., CNTF) or by grafting with fetal nigral neurons.

Ischemia-like conditions in vitro can be induced by culturing cells in medium purged with $N_2$ to deplete oxygen. Hippocampal neurons exposed to such conditions usually die within 24 hours. Similarly, an in vivo model for ischemia has been established by exposing rat neonates to nitrogen (Speiser et al., Behav. Brain Res. 7, 379–382 (1983)).

Many neurodegenerative processes, including motor neuron degeneration characteristic of amyotrophic lateral sclerosis (ALS), demonstrate an aberrant accumulation of neurofilaments in neurons. Transgenic mice having increased levels of neurofilament expression show morphologic features of motor neuron disease. A transgenic mouse containing a human genomic fragment encoding the neurofilament heavy (NF-H) gene can produce up to two-fold higher levels of NF-H protein than animals having the endogenous gene. By 3 to 4 months of age, NF-H transgenics progressively develop neurological defects and abnormal neurofilamentous swellings characteristic of ALS (Coté et al., Cell 75, 35–46 (1993)). In addition, Xu et al. (Cell 73, 23–33 (1993)) constructed transgenic mice expressing elevated levels of NF-L protein. In these animals, large motor neurons developed perikaryl neurofilament accumulations with phosphorylated NF-L. The number of degenerating axons increased and muscles innervated by large motor neurons exhibited severe atrophy coincident with the accumulation of perikaryal neurofilaments.

The polypeptides of the invention may be used to treat a variety of neurological disorders resulting from disease or injury to neural or non-neural cells. In particular, EBP may be used to protect or prevent degeneration of motor neurons as is commonly observed in ALS and spinal cord injuries. EBP may be used alone, or in combination with other neurotrophic factors such as ciliary neurotrophic factor (CNTF), brain derived neurotrophic factor (BDNF), glial derived neurotrophic factor (GDNF), nerve growth factor (NGF), insulin-like growth factor (IGF-1) or neurotrophin-3 (NT-3) for the treatment of motor neuron degeneration. EBP may also be used to protect or prevent loss of neural cell function associated with disease or injury affecting dopaminergic, pyramidal and noradrenergic neurons. Conditions associated with a decrease or loss of function of these neurons include Parkinson's disease, ischemia, or Alzhemier's disease. Other conditions treatable by EBP include Huntington's disease, multiple sclerosis, nerve trauma and peripheral neuropathies such as diabetic and chemotherapy-induced neuropathies. EBP may be used alone or in combination with other agents for treatment of these diseases.

EBP may also be used to maintain in culture the growth and/or differentiation of cells of the nervous system (neural cells and glial cells). EBP, or a biologically active analog or fragment thereof, may be added directly to an appropriate cell culture media. In particular, EBP may be used in culturing fetal neurons for transplantation into patients having damaged nervous system tissue. For example, embryonic dopaminergic neurons can be incorporated into adult brain and such grafts can alleviate behavorial disorders. Growth and/or differentiation in culture of other neurons can also be supported by addition of EBP.

The invention provides for pharmaceutical compositions comprising therapeutically effective amounts of an eck receptor ligand together with pharmaceutically acceptable diluents, carriers, preservatives, emulsifiers and/or solubilizers. A "therapeutically effective amount" as used herein refers to that amount which provides therapeutic effect for a given condition and administration regimen. It is expected that one skilled in the art would be able to determine a therapeutically effective amount of an eck receptor ligand for any given condition being treated.

Pharmaceutical compositions include diluents of various buffers (e.g., Tris, acetate, phosphate), solubilizers (e.g., Tween, Polysorbate), carriers such as human serum albumin, preservatives (thimerosol, benzyl alcohol) and anti-oxidants such as ascorbic acid. As shown in Example 7, the ability of purified and diluted EBP to bind to soluble eck receptor is prolonged when EBP is formulated in the presence of a stabilizing agent. The stabilizing agent may be a detergent, such as tween-20, tween-80, NP-40 or Triton X-100. EBP may also be incorporated into particulate preparations of polymeric compounds for controlled delivery to a patient over an extended period of time. A more extensive survey of components in pharmaceutical compositions is found in Remington's Pharmaceutical Sciences, 18th ed. A.R. Gennaro, ed. Mack, Easton, Pa. (1990).

EBP may be administered by injection, either subcutaneous, intravenous or intramuscular, or by oral or nasal administration. The route of administration will depend upon the particular condition being treated.

The following examples are offered to more fully illustrate the invention, but are not construed as limiting the scope thereof.

EXAMPLE 1

Production of eck receptor extracellular domain

A. Construction of an eck-x expression plasmid

A plasmid for mammalian expression of the extracellular domain of eck was generated in several steps beginning with pGEM3Z-eck, a 3.4 kb EcoRI-Kpn I subclone of the eck cDNA (Lindberg et al. supra). Oligonucleotides 317-11 (5'-AGCTTAGATCTCC-3'; SEQ. ID. NO. 7) and 317-12 (5'-AATTGGAGATCTA-3'; SEQ. ID. NO. 8) were kinased and ligated to the 1.7 kb EcoRI fragment of pGEM3Z-eck and pGEM4Z which had been digested with Hind III and EcoRI. A clone was selected which had the oligonucleotides added only to the 5' end of eck. Characteristics of this clone include the addition of Hind III and Bgl II sites and deletion of the 5' EcoRI site adjacent to the eck sequence. The insert from this clone was isolated following digestion with Hind III and EcoRI and ligated to kinased oligonucleotides:

```
317-9  5'-AATTCCAGACGCTGTCCCCGGAGGGATCCGGCAACTGAG-3'  (SEQ. ID. NO. 9)
and
317-10 5'-TCGACTCAGTTGCCGGATCCCTCCGGGGACAGCGTCTGG-3'  (SEQ. ID. NO. 10)
``` with pGEM4Z digested with Hind III and Sal I. This added a Bam H1 site, a TGA stop codon following Asn$^{534}$ and a Sal I restriction enzyme site. The Hind III-Sal I fragment containing the coding sequence for the external domain of eck was then transferred to pDSRα2 (deClerk et al. *J. Biol. Chem.* 266, 3893 (1991)).

B. Mammalian cell expression of eck x

The expression plasmid pDSRα-eck-x was introduced in CHO cells by calcium mediated transfection (Wigler et al. *Cell* 11, 233 (1977)). Individual colonies were selected based upon expression of the dihydrofolate reductase (DHFR) gene in the plasmid and one clone, designated 21.021 was chosen for amplification. Expression of the eck gene was monitored by RNA hybridization (Hunt et al. *Exp. Hematol.* 19, 779 (1991)).

Amplification of eck expression was done in 10 nM methotrexate. Cell line 21.02 was expanded for production of eck-x. Roller bottles were seeded at 2×10$^7$ cells in 200 ml DMEM:Ham's F12 (1:1) supplemented with non-essential amino acids, 10 nM methotrexate and 5% FBS. Cells reached confluence in 3 days at which time fresh media lacking 5% FBS was added. Conditioned media was harvested and replaced after seven days and a second harvest was taken after fourteen days.

C. Purification of eck-x

Conditioned medium from 21.02 cells was concentrated and diafiltered against 10 mM Tris-HCl, pH 7.4 using a 10,000 MWCO spiral wound filter (S1Y10, Amicon, Danvers, Ma). The 50 mL concentrate was loaded onto an anion exchange column (Hema-Q, 10 μm particle size, 1.6×12 cm, Separon, Sunnyvale, Calif.) and eluted with a linear gradient of 0–0.5 M NaCl in 10 mM Tris-HCL, pH 7.4. Fractions were analyzed by SDS-PAGE and western blotting using a rabbit antiserum generated against a synthetic N-terminal peptide of eck-x. Fractions containing eck-x were pooled, dialyzed against 10 mM Tris-HCl, pH 7.4, reloaded onto the Hema-Q column, and eluted and analyzed as before. The resulting pool was concentrated to 3 mL (centriprep-10, Amicon, Danvers, Mass.) and applied to a Superdex 200 (Pharmacia, Piscataway, N.J.) gel filtration column (2.2×90 cm, flow rate 1.0 ml/min) equilibrated in PBS. A pool containing the purified eck-x was made and served as the basis of further experiments.

EXAMPLE 2

Screening of conditioned media for binding to the eck extracellular domain

Interactions with eck-x were measured on a surface plasmon resonance detector system (BIAcore, Pharmacia Biosensor, Piscataway, N.J.) using procedures recommended by the manufacturer. The dextran surface of the sensor chip was activated by injecting 35 μl of 0.2M 1-ethyl-3-(3-dimethylaminopropyl)carbodiimide-HCl, 0.05M N-hydroxysuccinimide at a flow rate of 5 μl/min. The purified eck-x (0.2 mg/ml in 10 mM sodium acetate, pH 4.0) was immobilized by two consecutive 50 μl injections at 5 μl/min. Unreacted binding sites were blocked by injection of 1M ethanolamine, pH 8.5. The surface was washed overnight in running buffer (HBS, 10 mM Hepes, 150 mM NaCl, 3.4 mM EDTA, 0.005% Tween 20, pH 7.4) until a stable baseline was achieved. Typical immobilizations resulted in the establishment of baselines 6000–8000 response units above original values. 50 μl samples of various conditioned media, cultivated under serum free conditions and concentrated five- to forty-fold (centricon-10, Amicon, Danvers, Mass.), were injected at a flow rate of 10 μl/min. Sample response was measured at report points on the sensorgram corresponding to 20 seconds after the conclusion of each injection. The immobilized eck-x surface was regenerated between samples by 50 μl injections of 2 mM 3-(cyclohexylamino)-l-propanesulfonic acid, pH 10.4.

Purified eck-x immobilized on a BIAcore sensor chip was used to screen concentrated conditioned media for receptor binding activity. Binding activity was observed in several conditioned media, including those from HCT-8, SK-BR-3, and HT-29 cell lines. (see Table 1)

TABLE 1

Testing of cell culture supernatants by BIAcore and anti-EBP Western blot

| Cell line | Concentration | eck-x Binding Activity (BIAcore Response units) | Anti-EBP Western |
|---|---|---|---|
| A704 | 40x | 49 | – |
| TE671 | 40x | 115 | – |
| CCD18CO | 40x | 25 | – |
| CCFSTTG1 | 40x | 35 | – |

TABLE 1-continued

Testing of cell culture supernatants by BIAcore and anti-EBP Western blot

| Cell line | Concentration | eck-x Binding Activity (BIAcore Response units) | Anti-EBP Western |
|---|---|---|---|
| HCT-8 | 40x | 180 | ++ |
| GMO-0948 | 40x | 10 | – |
| SK-BR-3 | 40x | 270 | ++ |
| HT-29 | 40x | 310 | ++ |
| MDA-MB-453 | 30x | 80 | ++ |
| FF-1 | 30x | 55 | – |
| WS-1 | 25x | 55 | – |
| BRL-3A | 25x | 125 | – |
| GMO1391 | 25x | 20 | – |
| HT-1080 | 20x | 230 | + |
| AG-2804 | 20x | 170 | + |
| BUD-8 | 20x | –10 | – |
| AG-3022 | 20x | 175 | + |
| HFL-1 | 20x | 15 | – |
| LIM-1863 | 20x | 75 | – |
| PAEC | 20x | –10 | – |
| HOs | 10x | 95 | – |
| 33C0 | 10x | –10 | – |

Samples (50 μl injections) were tested for binding to immobilized eck-x using BIAcore, as described in Example 2. Aliquots (10 μl) of the same samples were analyzed retrospectively with rabbit anti-EBP (*E. coli*) antiserum.

EXAMPLE 3

Purification and Characterization of an eck receptor binding protein (EBP) from conditioned medium A. Immobilized eck-x receptor affinity chromatography.

Purified eck-x was dialyzed against 0.1M NaHCO$_3$, 0.5M NaCl, pH 8.3 and brought to a final concentration of 2 mg/ml. The protein was immobilized on CNBr-activated Sepharose 4B (Pharmacia, Piscataway, N.J.) at a ligand density of 1 mg eck-x per ml of gel (Kenny et al. in *New Protein Techniques*, J. M. Walker, ed. The Humana Press, Clifton, N.J. (1988)).

Conditioned medium from SK-BR-3 or HCT-8 cell lines was concentrated twenty fold and diafiltered against PBS (S1Y10 spiral cartridge, Amicon). The concentrate was loaded directly onto columns of immobilized eck-x (1×1 cm, 1mg eck-x per ml resin) at a flow rate of 0.1 ml/min. The column was washed with 10 ml of PBS, followed by elution with 0.05 M sodium acetate, 0.5 M NaCl, pH 4.0. The elution pool was brought to 0.01% SDS, concentrated, and buffer exchanged against 10 mM Tris-HCl, pH 8.0 in a centricon-10 ultrafiltration device (Amicon). Samples were mixed with SDS-PAGE sample buffer, harvested from the centricon-10, and loaded directly onto polyacrylamide gels. Gels were stained with silver (Merrill *Meth. Enzymol.* 182, 477 (1991)) or blotted onto PVDF membranes (Problot, Applied Biosystems, Foster City, Calif.) for N-terminal sequence analysis (Fausset et al. *Electrophoresis* 12, 22 (1991)).

An SDS-PAGE analysis of a typical run is shown in FIG. 1. The pH 4.0 elution of the column, shown in lane 5, displays a significant enrichment for several proteins with apparent molecular weights of 21–27 kDa. These proteins were not detected when a similar volume of unconditioned medium was passed over the same column, indicating that the 21–27 kDa proteins were produced by the cell lines. In contrast, the higher molecular weight proteins present in the pH 4.0 elution fractions of HCT-8 or SKBR-3 conditioned medium were also observed in the unconditioned medium. These proteins represent nonspecific interactions with the column, and originate from the serum used for cell culture.

B. N-terminal sequence analysis of EBP.

N-terminal sequence analysis was performed on a liquid-pulse automatic sequencer (model 477, Applied Biosystems, Foster City, Calif.). The resulting phenylthiohydantoinyl amino acids were analyzed by on-line microbore high performance liquid chromatography (Model 123, Applied Biosystems) using a Brownlee C-18 reverse-phase column (0.21×25 cm). The sequencing cycles and optimization for sequence analysis of PVDF blots were based on recommendations supplied by Applied Biosystems.

N-terminal sequence analysis of the electroblotted proteins in the 21–27 kDa region of the gel revealed a single sequence (SEQ. ID. NO. 14):

NH$_2$-Asp-Arg-His-Thr-Val-Phe-Trp-[Asn]-Ser-Ser-Asn-Pro-Lys-Phe-Arg-Asn-Glu-Asp-Tyr-Thr-Ile-His-Val-Gln

A computer based homology search of the NBRF protein database (Devereux et al. *Nucleic Acids Res.* 12, 387 (1984)) resulted in the unambiguous assignment of this sequence to EBP (Holzman et al. supra).

C. Structural characterization of EBP.

Since N-terminal sequencing detected a single sequence, the multiple forms of EBP observed by SDS-PAGE probably arise from post-translational modifications at other regions of the molecule. The sequencing yield of cycle 8 (N) was greatly diminished, indicating efficient glycosylation at this site. However, the apparent heterogeneity of the protein may not be fully attributable to glycosylation differences, since digestion of rEBP with combinations of N-glycanase, neuraminidase, and O-glycanase resulted in a mixture of forms with Mr 17–19 kDa, when analyzed by SDS-PAGE. Since the EBP gene codes for a protein of 22 kDa (Holzman et al. ibid), this observation suggested that EBP might be subject to proteolytic processing.

D. Interactions of EBP with soluble eck receptor.

Figure 2:
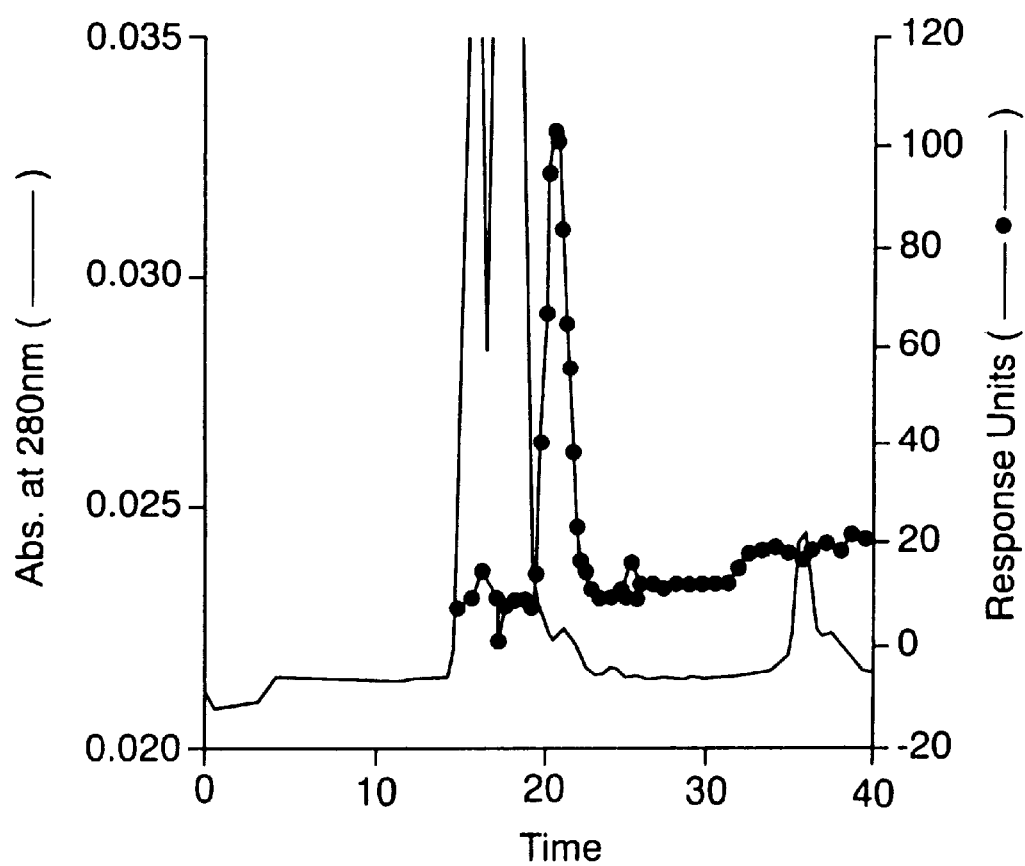
FIG. 2. Gel Filtration analysis of purified EBP from HCT-8 cell line. EBP, purified by immobilized eck-x receptor affinity chromatography, was amended with 50 $\mu$g/ml BSA and injected onto a Superdex 75 column. Fractions were tested for eck-x binding activity by BIAcore.

Gel filtration analysis of the pH 4.0 eluted pool demonstrated that all of the eck-binding activity, as measured by BIAcore response, could be attributed to material eluting with apparent molecular weight of 22 kDa (FIG. 2). SDS-PAGE analysis of the fractions from this column confirmed that EBP was co-eluted with the receptor binding activity. In separate experiments, purified EBP did not bind to BIAcore surfaces activated with the extracellular domain of the kit receptor, although these surfaces could bind rSCF, the kit ligand.

E. Screening of additional cell lines for eck binding proteins.

Following the isolation and identification of EBP, antiserum to the protein was prepared, and a retrospective analysis of the original screening was performed (Table 1). Western blot analysis confirmed that EBP was present at high levels in three conditioned media (SK-BR-3, HCT-8, and HT-29) which scored positive in the screening. Several other cell lines (AG-3022, AG-2804, and HT-1080) scored positive, but only trace amounts of processed EBP could be detected by the Western analysis. These cell lines did produce a 28 kDa protein which was detected by the anti-EBP antiserum.

EXAMPLE 4

Cloning, Expression and Characterization of EBP

Heat-disrupted phage from a human umbilical vein endothelial cell (HUVEC) library (Clontech Laboratories, Palo Alto, Calif.) were used as a template for amplification of the human EBP gene by polymerase chain reaction (PCR) (Saiki et al. *Science* 2, 1350 (1985); Mullis et al. Cold Spring Harbor *Symp. Quant. Biol.* 51, 263). Primers were designed based on the published nucleic acid sequence of EBP (Holzman et al. ibid) to yield PCR fragments that could be inserted into either *E. coli* or CHO cell expression vectors.

A. Cloning of EBP for *E. coli* Expression

A gene for *E. coli* expression of the full length form of EBP was generated by PCR using oligonucleotide primers 386-4 and 386-5 as shown below:

```
386-4) 5' AAG CAT ATG GAT CGC CAC ACC GTC TTC TGG 3'     (SEQ. ID. NO. 2)

386-5) 5' GAA GGA TCC TTA TCA CGG GGT TTG CAG CAG CAG    (SEQ. ID. NO. 3)
          AA 3'
```

This form lacked the signal peptide and included an initiator methionine as well as restriction sites necessary for cloning into the expression plasmid pCFM1156 (Fox et al. *J. Biol. Chem.* 263, 18452 (1988)). A 10 μl aliquot of the λ gt11/HUVEC library (Clontech) was heat treated at 700° C. for 5 minutes then quick-cooled on wet ice. The disrupted phage were used as the template for a PCR reaction containing 300 picomoles each of primers 386-4 and 386-5, 1X TaqI polymerase buffer (Promega, Madison, Wis.), 0.77 mM of each dNTP, and 2.5 units of TaqI polymerase (Promega) in a volume of 100 μl. The product of this reaction was extracted with phenol/chloroform, ethanol precipitated, resuspended in 20 μl of distilled water and then digested with the restriction endonucleases NdeI and BamHI (Boehringer Mannheim, Indianapolis, Ind.). This fragment was ligated into the plasmid vector pCFM1156 which had been digested with the same two enzymes and transformed into the *E. coli* host strain FM5 (A.T.C.C. No. 53911). When transformed cells were temperature shifted from 30° C. to 42° C., EBP was expressed at high levels.

A gene designed to express the 150 amino acid form of EBP in *E. coli* was constructed as described for the full-length gene except that oligonucleotide 469-11 was used in mCR instead of 386-5. Oligonucleotide 469-11 has th e sequence:

```
                                                         (SEQ. ID. NO. 4)
5' GAAGGATCCCTATTATGCTGCAAGTCTCTTCTCCTG 3'
```

B. Cloning of EBP for CHO cell expression

Total RNA was isolated from the cell line SK-BR-3, and used to prepare cDNA. Three μg of total RNA was mixed with 3 μg of random primer (Gibco BRL, Gaithersburg, Md.), incubated at 65° C. for 5 min, then cooled briefly on ice. The RNA-primer mixture was then used in a cDNA reaction which consisted of 50 mM Tris-HCl (pH 8.3), 75 mM KCl, 3 mM MgC$_2$, 10 mM DTT, 125 μM of each dNTP (dATP, dCTP, dGTP, dTTP), 200 units of reverse transcriptase (Superscript, BRL), in a final reaction volume of 20 μl. The reaction was incubated at 37° C. for 1 h.

Two oligonucleotides were synthesized and used with the SK-BR-3 CDNA to amplify the EBP coding region by PCR.

```
386-2) 5' GAA TTC AAG CTT CAG GCC CCG CGC TAT GGA G 3'    (SEQ. ID. NO. 5)

386-3) 5' GAA TTC TCT AGA TCA TCA CGG GGT TTG CAG CAG    (SEQ. ID. NO. 6)
          CA 3'
```

The PCR contained 1 μl of the cDNA reaction, 500 ng of both of the above oligonucleotides, 10 mM Tris-HCl (pH 8.3), 50 mM KCl, 200 μM of each dNTP, and 1.25 units of Taq polymerase (Perkin Elmer Cetus, Calif.). DNA was amplified for 35 cycles (94° C. for 30 s, 50° C. for 1 min, 72° C. for 1 min), extracted 1 time with phenol, 1 time with phenol-chloroform, precipitated, pelleted by microcentrifugation, and digested with the restriction enzymes Hind III and Xba I (Boerhinger Mannheim). The DNA was gel-purified (Geneclean II, Bio 101, La Jolla, Calif.) and ligated to the plasmid pDSRα2 (deClerck et al., ibid) which had been previously digested with the same restriction enzymes. The ligated DNA was transfected into competent HB101 bacteria (BRL), and plasmid DNA was isolated (Qiagen, Chatsworth, Calif.). The DNA sequence was confirmed by the dideoxy chain termination reaction (Sanger et al. *Proc. Natl. Acad. Sci. USA* 74 5463 (1977)) on double-stranded plasmid DNA using synthetic primers that corresponded to the EBP DNA sequence.

Culture supernatants from CHO cells transfected with the EBP gene displayed eck-x binding activity on the BIAcore, and EBP could be recovered from the supernatants by immobilized eck-x receptor affinity chromatography. Untransfected CHO cells, or CHO cells transfected with a EBP gene containing an internal deletion, displayed no receptor binding activity.

C. Purification of recombinant EBP from *E. coli* and CHO cells

Recombinant EBP was purified from CHO cell culture supernatants by immobilized eck-x receptor affinity chromatography as described in Example 3A. The purified EBP was dialyzed vs. PBS with either 5 mM CHAPS (for structural analysis and crosslinking studies) or 0.5 mg/ml BSA (for phosphorylation studies). The CHO cell-derived EBP purified by receptor affinity chromatography contained two major bands, as well as a few minor bands (FIG. 1B).

Recombinant EBP from CHO cells was also purified by conventional chromatography. The CHO cell culture supernatant was concentrated and diafiltered. against 10 mM Tris, pH 8.5 and applied to an anion exchange column (Q-Sepharose, Pharmacia-LKB). The column was eluted with a linear gradient of NaCl in 10 mM Tris-HCl, pH 8.5. Analysis of the fractions by western blotting showed that the two major EBP bands had been separated from one another. Separate pools were made of fractions containing the major EBP bands, and the pools were further purified by gel filtration chromatography (Superdex-75, Pharmacia-LKB) Recombinant EBP from *E. coli* was purified by the following method. Cells expressing the EBP$^{1-150}$ or EBP$^{1-187}$ genes were suspended in 10 mM Tris-HCl, pH 7.4 and lysed using a French press. The lysate was centrifuged in a J6-B (JS-4.2 rotor) at 4000 rpm for 30 min. The insoluble pellets (containing either unfolded EBP$^{1-150}$ or EBP$^{1-187}$) were saved for further processing. The pellets were suspended in 2% sodium deoxycholate, 5 mM EDTA, 10 mM Tris-HCl, pH 8.5, and mixed for 30 minutes at 4° C. The suspensions were centrifuged as above, and the supernatants discarded. The insoluble pellets were suspended in 10 mM Tris-HCl, pH 7.4, mixed, and centrifuged as above. The insoluble pellets were dissolved in 2% sarkosyl, 10 mM CAPS, pH 10 in order to solubilize EFBP$^{1-150}$ or EBP$^{1-187}$. CuSO$_4$ was added to a final concentration of 50 μM, and the mixtures were stirred overnight at 4° C., then treated with Dowex 1×4 resin in order to remove the detergent.

SDS-PAGE analysis revealed that a large proportion of EBP$^{1-150}$ or EBP$^{1-187}$ had oxidized and was monomeric. However, gel filtration analysis of EBP$^{1-187}$ showed that the protein behaves as a high molecular weight noncovalent aggregate. In contrast, gel filtration analysis indicates that the refolded EBP$^{1-150}$ behaves as a monomer or dimer.

EBP$^{1-187}$ and EBP$^{1-150}$ produced in *E. coli* were tested for binding to immobilized eck-x by BIAcore as described in Example 2. The EBP$^{1-187}$ aggregate bound poorly, if at all, to the eck-x surface. Refolded EBP$^{1-150}$ demonstrated high affinity for eck-x surfaces on the BIAcore.

Alternatively, the following procedure was used to re-fold EBP$^{1-150}$ expressed in *E. coli*. Cell paste was suspended in 9 volumes (v/w) of cold Super-Q water. The suspended cell paste was lysed using a Gaulin homogenizer at a pressure of 9,000 psi. The lysate was immediately centrifuged at 3,500× G, 4° C. for 30 minutes. The supernatant was discarded and the pellet, containing EBP inclusion body, was saved. The pellet was suspended in 10 volumes (v/w) of 8M urea, 0.1M Tris, pH 8.5, and stirred for one hour. Centrifugation was then performed to remove the insoluble fraction. Refolding was effected by two stepwise dilutions of the soluble inclusion body. First, the inclusion body was diluted into 10 volumes (v/w) of 3M urea, 0.1M Tris, pH 8.5, containing 0.0005% CuSO$_4$ as a oxidizing agent, at 4° C. while stirring overnight. This material was diluted with 3 volumes (v/v) of 20 mM Tris, pH 9.2, and was incubated for 24 hrs with gentle stirring. Centrifugation was performed at 15,000×G, 4° C. for 30 minutes to remove precipitate.

The supernatant was then applied into Q-Sepharose Fast Flow column and washed with five column volumes of 20 mM Tris, pH 9.2. The column was eluted with a linear gradient of NaCl from 0–0.5M in 20 mM Tris, pH 9.2. Fractions containing EBP were pooled, concentrated, and subjected to Superdex-75 chromatography. The EBP was eluted with 1X PBS.

The resulting purified EBP had a specific activity that is 30–40% of purified CHO derived EBP as measured by its ability to bind to immobilized eck-x in a BIAcore assay. The E.coli produced EBP refolded and purified by this procedure induced the phosphorylation of eck localized on cellular surfaces.

D. Characterization of recombinant EBP from *E. coli* and CHO cell expression

Recombinant EBP, purified by receptor chromatography from CHO cell culture supernatants, or by RP-HPLC from *E. coli* was digested with trypsin and analyzed by RP-HPLC. Although the C-terminal peptide (aa 155–187) was recoverable from the EBP$^{1-187}$ gene expressed in *E. coli*, it could not be detected in the mammalian derived recombinant protein. Carboxypeptidase digestion of the purified CHO EBP indicated that the only detectable C-terminal sequence was -lys-arg-leu-ala-ala-COOH (SEQ. ID. NO. 13), indicating a terminus at amino acid 150.

E. Alternative Forms of EBP

EBP isolated from SK-BR-3 cell line as described in Example 3 migrated on SDS-PAGE in the range of 21–27 kDa (see FIG. 1A). Recombinant EBP in CHO cell supernatants existed as two major species and a few minor bands after eck-x chromatography (Example 4 and FIG. 1B). Further characterization of the different molecular weight forms of CHO-derived EBP was undertaken. Purification of recombinant EBP from CHO cell supernatants revealed two bands of 22 and 24 kDa and a third minor band of 27 kDa (see FIG. 3). Treatment of purified EBP with glycosidases did not change the relative migration of these bands suggesting that they did not arise simply by variation in N- or O-linked carbohydrate. C-terminal sequencing previously revealed the 22 kDa band as a polypeptide of 150 amino acids designated EBP$^{1-150}$. The 24 kDa band was found to be 159 amino acids long as evidenced by C-terminal sequencing. This form was designated EBP-$^{1-159}$.

Figure 4:
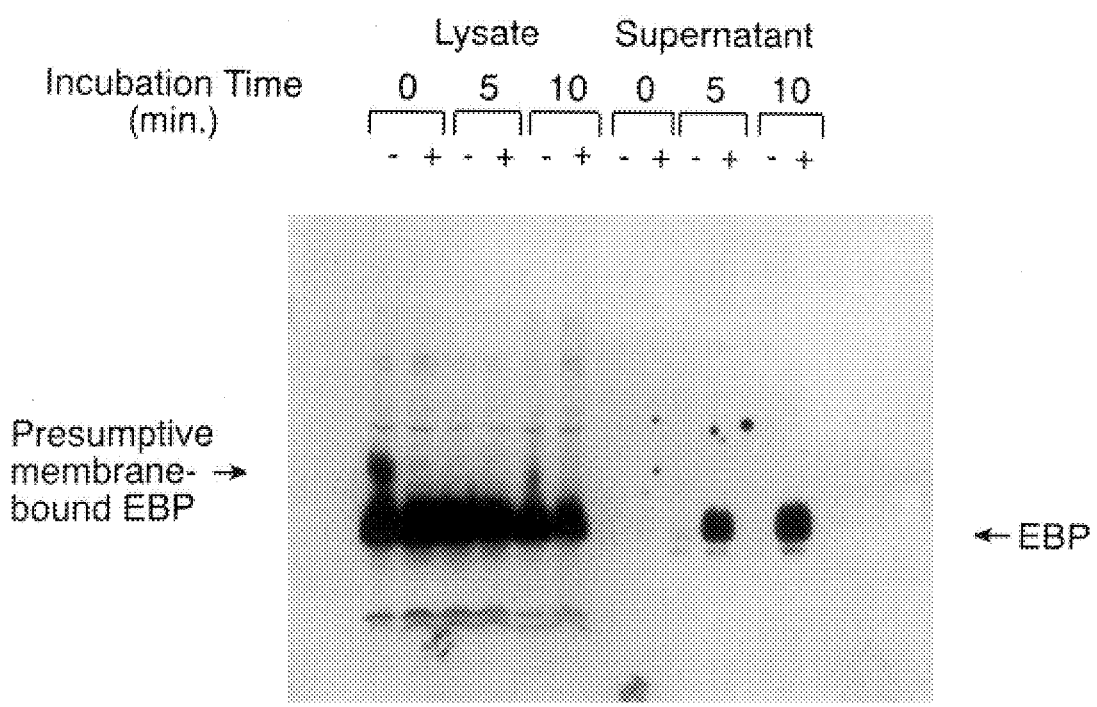
FIG. 4. Analysis of release of membrane-bound EBP from CHO cell surfaces by phospholipase C treatment. "−" indicates incubation in the absence of phospholipase C; "+" indicates incubation in the presence of phospholipase C. Time of incubation was 0, 5 and 10 minutes.

CHO cells expressing EBP were studied for the presence of membrane-bound forms of EBP. The recombinant CHO cell line 36.44 was established by transfection of CHOd- cells with the plasmid pDSRα-EBP. Cells were grown in suspension media using DMEM:F12 media supplemented with 1X non-essential amino acids and 1X penicillin, streptomycin, glutamine with 10% heat inactivated dialyzed fetal bovine serum. Aliquots of 10$^6$ cells were treated with 4 μg/mL phospholipase C (Calbiochem, La Jolla, Calif.) in lmL phosphate buffered saline at 37° C. for various times. Cells were pelleted at 14,000 RPM for 1 minute. Supernatants were removed for analysis. Cell pellets were lysed in RIPA buffer (150 mM NaCl; 1% NP-40; 0.5% deoxycholate; 50 mM Tris-HCl pH 8.0; 0.1% SDS; 1.74 μg/mL PMSF; 1 ng/mL each of aprotinin, pepstatin and leupeptin; 18.4 μg/mL orthovanadate). Samples were applied to a 14% Tris-Glycine gel, blotted to a PVDF membrane and probed with a rabbit anti-EBP polyclonal antibody. FIG. 4 shows that EBP was released into the supernatant in the presence of phospholipase C. These experiments suggested that the 27 kDa form of EBP had a glycophospholipid anchor.

EXAMPLE 5

EBP Analogs

In addition to the different forms of recombinant EBP made from the full-length EBP gene, analogs of EBP were constructed having varying polypeptide lengths. In particular, EBPs having 167, 171 and 180 amino acids were constructed as follows. Oligonucleotides 421-12, 421-13 and 421-14 were synthesized for use as PCR primers to introduce termination codons following amino acid 180, 171 and 167, respectively. PCR reactions were done as described in Example 4B using each of those primers and the pDSRα-EBP plasmid and oligonucleotide 386-2.

```
421-12 5'-GAATTCTCTAGATTATCATGGAAGGAGCAGCACAGTCCAG-3'   (SEQ. ID. NO. 15)

421-13 5'-GAATTCTCTAGATTATCATGGGAAGAGGCGTGGGGCAGC-3'    (SEQ. ID. NO. 16)

421-14 5'-GAATTCTCTAGATTATCATGGGGCAGCACTGTGACCGATGC-3'  (SEQ. ID. NO. 17)
```

The resulting analogs were expressed in CHO cells transfected with the altered DNA sequences using procedures described for the expression of EBP. Cells were grown to confluence in the presence of serum whereupon the media was switched to serum-free and allowed to accumulate. At 48 hours the conditioned medium was collected and the adherent cells were lysed. Aliquots of the conditioned media and lysates were fractionated by polyacrylamide gel electrophoresis and subjected to Western blotting. EBP-$^{1-187}$ and EBP$^{1-180}$ displayed a similar distribution of protein reacting with the antibody in lysates and supernatants. Cells expressing EBP$^{1-170}$ and EBP$^{1-187}$ had accumulation of EBP in the supernatants, but not in the lysates. EBP analogs are analyzed for binding to eck-x by BIAcore as describe in Example 2 and for phosphorylation activity of eck receptor as described in Example 6.

EXAMPLE 6

Interactions of recombinant EBP with the eck receptor

A. Crosslinking studies.

CHO-cell derived EBP was radiolabelled with $^{125}$I as described below for use in crosslinking and binding studies. Five or 10 μg of EBP in 0.1M sodium phosphate (NaPO$_4$, pH 8.0) was added to 5 mCi of dried $^{125}$I-Bolton-Hunter reagent (NEN, Boston, Mass.) in a final volume of 50 μl or 100 μl, and the tube was incubated at 4° C. for 1 h. The reaction was terminated by addition of 0.3 ml of 0.2M glycine in 0.1M NaPO$_4$, followed by incubation at 4° C. for 5 min. Labeled protein was separated from unincorporated reagent by gel filtration chromatography on a 10 ml PD10 column containing Sephadex G-25 M (Pharmacia) equilibrated with 0.1M NaPO$_4$— 0.25% gelatin. Specific activity of the $^{125}$I-EBP ranged from 4 to 19 cpm/pg.

Crosslinking of EBP to either LIM 2405 (a cell line naturally expressing the eck receptor) or CHO 19.32 (Chinese hamster ovary cells transfected with a clone of the full length eck receptor) was carried out as follows. CHO cells were grown in suspension to a density of approximately 5×10$^5$ cells/ml in media. LIM2405 cells were grown in RPMI 1640 media containing 5% FCS, 1 μg/ml insulin, 1 μg/ml hydrocortisone, 10 pM thioglycerol and 2 mM L-glutamine to approximately 90% confluency in T-175 flasks and removed by scraping for use in the crosslinking studies. Cells were spun down and resuspended in PBS to give a single cell suspension. For each crosslinking reaction, 2×10$^6$ cells were mixed with approximately 20 ng of $^{125}$I-EBP in a total volume of 1 ml. This mixture was incubated at 4° C. for 1 h to allow binding of EBP to cell surface receptors before the addition of 20 μl of 10 mM disuccinimidyl suberate (DSS) as a crosslinking agent. Cells were then washed three times in binding buffer, collected by centrifugation, and the amount of radioactivity incorporated into the cell pellets was counted to assess the degree of crosslinking. The cells were then lysed by treatment with 100 μl PBS, 1 mM EDTA, 0.5% NP-40, 1 mM phenylmethylsulfonyl fluoride (PMSF, Sigma, St. Louis, Mo.) for 10 min at 40° C. The insoluble material was removed by centrifugation and the soluble fraction containing the receptor/ligand complex was collected. These samples were either run directly on SDS-PAGE or first immunoprecipitated with an antibody directed against the C-terminal portion of the eck receptor (Lindberg et al. supra). Competition with either unlabeled EBP or an irrelevant protein (FGF) was carried out by mixing the competitor with the labeled EBP prior to addition to the cells.

Figure 5:
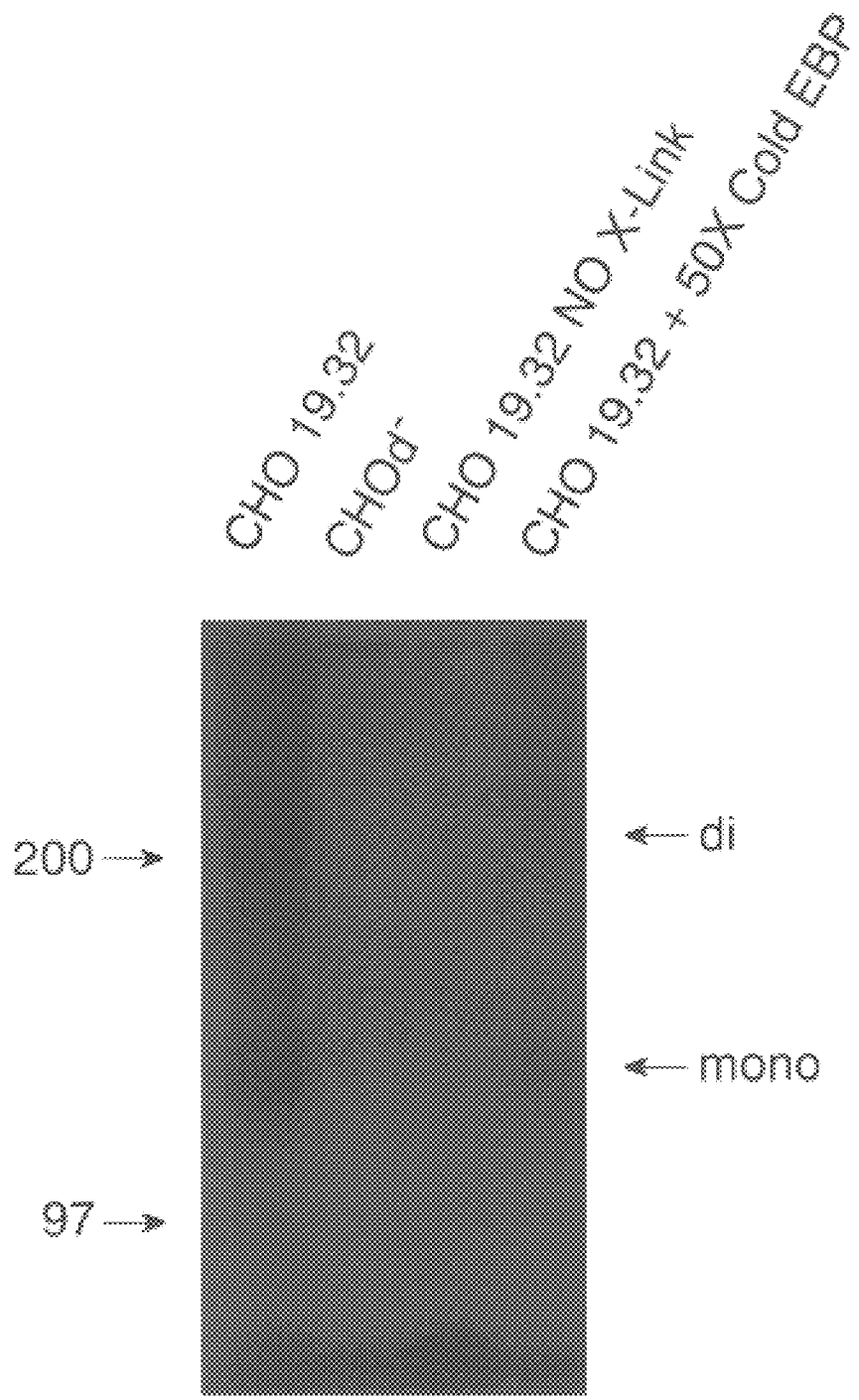
FIG. 5. Chemical crosslinking of $^{125}$I-rEBP to CHO 19.32 cells expressing eck. Cells were treated as described in Example 5. Lane 1, $^{125}$I-rEBP+CHO 19.32 Lane 2, $^{125}$I-rEBP+CHOd- (untransfected). Lane 3, $^{125}$I-rEBP+CHO 19.32, no crosslinker added. Lane 4, $^{125}$I-rEBP+CHO 19.32+50× unlabelled rEBP.

As shown in FIG. 5, $^{125}$I-rEBP could be crosslinked to CHO 19.32 cells (lane 1) but not to the untransfected cells (lane 2). Crosslinking resulted in the detection of a 145 kDa protein, as well as higher molecular weight forms which may represent receptor dimers or higher order complexes. Unlabelled rEBP at 50-fold molar excess was able to compete for binding and crosslinking (lane 3). In separate experiments, recombinant fibroblast growth factor at concentrations of 1 μg/mL had no effect on rEBP crosslinking. Similar crosslinking results were obtained for the LIM 2405 cell line.

B. Binding studies.

To measure association kinetics, CHO 19.32 cells (2×10$^6$ cells/ml) were incubated with 3.8 nM $^{125}$I-EBP in PBS-BSA (1 mg/ml), at 0° C. Aliquots were removed, and cell-bound $^{125}$I-EBP was determined by centrifugation through sucrose gradients. Nonspecific binding was measured from parallel reactions containing 380 nM unlabelled EBP.

Equilibrium binding constants were determined by incubating CHO 19.32 or LIM 2405 cells (0.5×10$^6$ cells/ml) with varying amounts of $^{125}$I-EBP at 0° C. for 1 h, bound EBP was determined as above, and the data was analyzed by the method of Scatchard (*Annal. N.Y. Acad. Sci.* 51, 660 (1949)). Nonspecific binding was determined from parallel reactions containing a 50 fold excess of unlabeled EBP.

A Scatchard analysis of the steady-state binding of $^{125}$I-rEBP to LIM2405 cells revealed that there was apparently a single class of receptors on the cell surface with a K$_d$ of 2.8×10$^{-8}$ M±0.3×10$^8$. On average, the LIM2405 cells contained 1.3×10$^6$ EBP receptors at the cell surface. BIAcore analysis of EBP binding to immobilized eck-x surfaces resulted in an estimated K$_d$ of 2.4×10$^{-8}$ M±0.4×10$^{-8}$.

C. p130$^{eck}$ autophosphorylation studies.

The LIM 2405 colorectal carcinoma cell line (Whitehead et al. *Immunol. and Cell Biol.* 70, 227 (1992)) was maintained in RPMI 1640 containing 5% FBS, 1 μg/ml insulin, 10 μg/ml hydrocortisone and 10 μM α-thioglycerol, and subpassaged by trypsination and dilution (1:5) into fresh media. Prior to assay 2.5×10$^5$ LIM 2405 cells were seeded into 6-well dishes (Falcon # 3046) and incubated for 24 hr at 37° C. The media was discarded and replaced with serum-free RPMI 1640 containing 0.03% BSA, 1 μg/ml insulin, 10 μg/ml hydrocortisone and 10 μM α-thioglycerol, then incubated for 12–18 hr. In some experiments the cell cultures were labelled with $^{32}$P-orthophosphate (2 mCi/ml) in phosphate-free RPMI 1640 (Flow) for 2-3 hr prior to treatment. Growth factor stock solutions were prediluted at varying concentrations into 2.0 ml of serum-free media, then warmed to 37° C. Cell cultures were removed from the incubator, and the supernatant media discarded. Treatments were promptly added and the cell cultures incubated at 37° C. for 10–15 min. The cultures were then removed from the incubator, placed on ice, and the culture supernatant aspirated.

The treated cell cultures were chilled to 0° C. then washed once with ice-cold PBS (GIBCO). The residual PBS was aspirated and the cells were lysed by the addition of 1.0 ml of ice-cold RIPA buffer (10 mM sodium phosphate, pH 7.4, 150 mM sodium chloride, 0.1% sodium dodecyl sulfate, 1% NP-40, 1% deoxycholate, 1% Trasylol, 2 mM EDTA, 50 mM sodium fluoride and 100 mM sodium orthovanadate). After a 10 min incubation the lysates were transferred to 1.5 ml tubes and clarified by centrifugation for 30 min at 10,000×g. The clarified lysate supernatants were transferred to new tubes and immunoprecipitated with 1.0 µg/ml of affinity purified rabbit anti-Eck C-terminal domain antibody for 2 hr at 0° C. Immune complexes were adsorbed to Protein-G Sepharose beads (Pharmacia) at 4° C. for 30 min, washed twice with ice-cold RIPA buffer, once with 0.1 M Tris-Hcl HCl, pH 8.0, containing 0.5 M LiCl, and once with RIPA. The resulting immunoprecipitates were solubilized with SDS-PAGE sample buffer and stored for further analysis.

The anti-eck immunoprecipitates from treated and untreated LIM 2405 cell lysates were resolved on 7.5% polyacrylamide gels as previously described (Boyle et al. Meth. Enzymol. 201, 110 (1991)). After electrophoresis, the gels were electroblotted (Kamps Meth. Enzymol. 201, 110 (1991)) onto Immobilon P (Millipore) and the blots were incubated for 1 hr in Tris-buffered saline containing 0.1% Tween-20 (TBST) and 5% BSA to block non-specific binding sites on the membrane. Primary antibodies, either anti-phosphotyrosine antibody (4G10, UBI, Lake Placid, N.Y.), or anti-eck C-terminal, were diluted to 1.0 µg/ml in TBST containing 3% BSA, 1% ovalbumin and incubated with the blots for 1 hr at room temperature. After this, the blots were rinsed with TBST, then washed once for 10–15 min, then twice for 5 min, each with TBST. The blots were then incubated with a 1:5000 dilution of secondary antibody coupled to horseradish peroxidase (Amersham, Arlington Heights, Ill.) in TBST alone for 20–30 min, then washed as before using TBST. Immune complexes were detected by chemiluminescent exposure (ECL, Amersham) to Kodak X-OMAT X-ray film at room temperature for 0.5–5 min.

Figure 6:
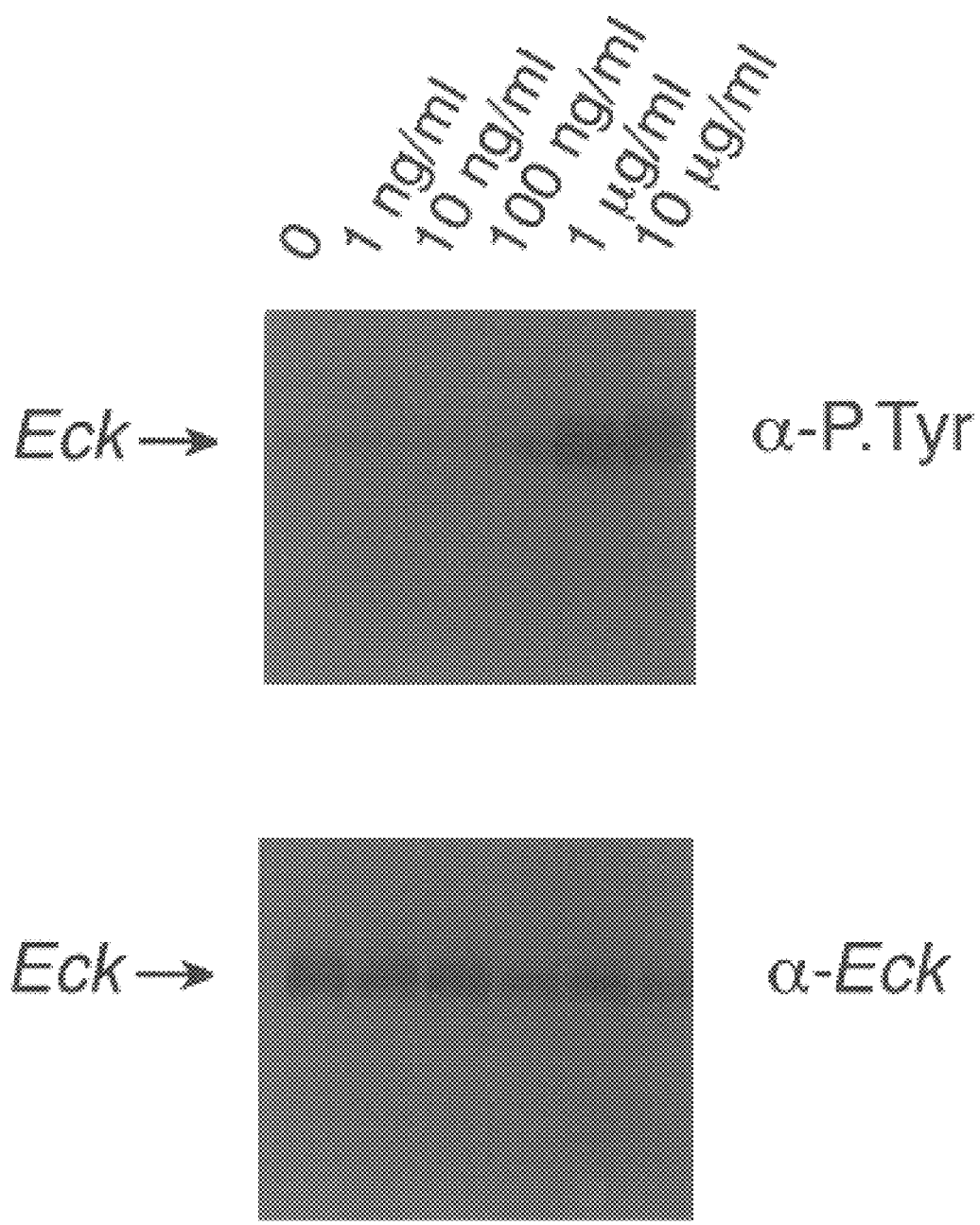
FIG. 6. Activation of the eck receptor tyrosine kinase in LIM 2405 cells treated with purified rEBP. Serum-starved LIM 2405 cells were treated for 10–15 min at 37° C. with increasing concentration of purified rEBP (CHOd-/EBP). The treated cells were lysed and then immunoprecipitated with anti-eck C-terminal antibody. The immunoprecipitates were split into two equal samples and resolved in parallel in a 7.5% SDS polyacrylamide gel. The gel was blotted onto membrane, then probed with either monoclonal anti-phosphotyrosine antibody (upper panel) or anti-eck C-terminus (lower panel). Migration of the eck polypeptide is marked by an arrowhead.

Eck receptor immunoprecipitates from $^{32}$P-labelled LIM 2405 cells were resolved by SDS-PAGE, and the gel dried directly without fixation. After exposure to X-ray film the labelled eck receptor band was isolated and phosphoamino acid content determined as described (Boyle et al. Meth. Enzymol. 201, 110 (1991)) CHO cell-derived rEBP stimulated eck receptor phosphorylation in intact LIM 2405 cells in a dose-dependent manner, with an optimal concentration between 100 ng/ml and 1 mg/ml (FIG. 6, upper panel). There also appeared to be a modest dose-dependent decrease in the total cellular eck protein levels (FIG. 6, lower panel), suggesting down regulation of the receptor after exposure to soluble EBP. Treatment of LIM 2405 cells with EBP does not result in spurious phosphorylation of the EGF receptor, nor does EGF treatment induce eck phosphorylation. Furthermore, when total cellular protein from LIM 2405 cells treated with rEBP was analyzed, the only induced phosphoprotein is a Mr 130 kd polypeptide that corresponds to the mature eck receptor.

rEBP$^{1-150}$ from E. coli was also assayed for autophosphorylation of the eck receptor on LIM 2405 cells following the procedure used for CHO-cell derived rEBP. Upon treatment of cells with the same quantities of CHO-derived rEBP and E. coli derived EBP$^{1-150}$, it was observed that both forms of recombinant EBP were active in inducing phosphorylation.

EXAMPLE 7

Formulation of Recombinant EBP

Figure 7:
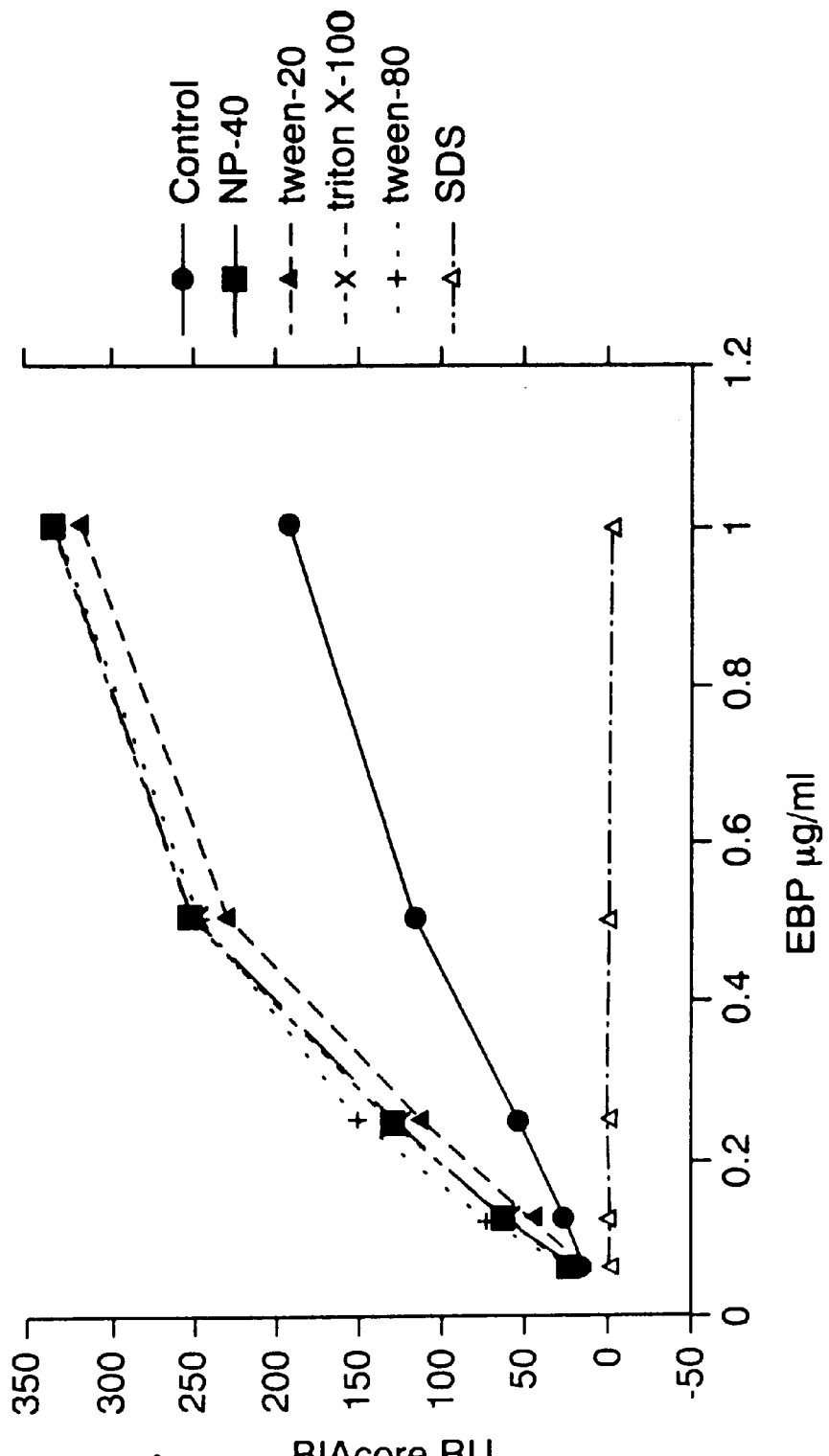
FIG. 7. Binding of CHO-derived EBP in various detergent formulations to immobilized eck receptor as measured by BIAcore. Purified EBP was diluted to 100 $\mu$g/ml in PBS in the presence or absence of detergent and incubated for 2 hrs. at 3° C. Protein samples were diluted to the concentrations indicated in the figure and tested for eck receptor binding.

Measuring the ability of EBP to bind to the immobilized soluble extracellular domain of eck using BIAcore, it was determined that dilute solutions of purified EBP rapidly lost the ability to bind to the eck receptor unless formulated with a protective agent such as a detergent. Recombinant CHO EBP diluted into PBS to 100 µg/ml and incubated for 2 hours at 3° C. lost approximately 50% of its eck binding activity. This loss of activity can be avoided by formulating the EBP in a detergent such as 1 mM CHAPS, 0.1% NP-40, 0.1% tween 20, 0.1% triton-X 100, or 0.1% tween 80. (see FIG. 7). The loss of eck binding activity in diluted EBP can also be avoided by incubating the protein with other protein carriers such as fetal calf serum.

The eck binding activity of at EBP 2–5 mg/ml kept in detergent solutions is stable for at least one week at 3° C., but protein solutions in the 10–500 µg/ml range will lose activity if stored at −20° C., or if they are subjected to multiple freeze thaw cycles.

EXAMPLE 8

Expression of EBP and eck receptor in tissues and cell lines

Expression of EBP has been studied at the mRNA level in various rat tissues and organs using procedures described in Lindberg et al., supra. EBP is expressed most highly in the lung, intestine, liver, ovary and kidney. Expression was also detected at lower levels in muscle, stomach, and brain.

Expression studies have been done for both EBP and the eck receptor in cell lines. EBP expression was tested for by immunoblotting cell supernatants in a Western analysis with affinity purified anti-human EBP monoclonal antibodies. As shown in Table 2, EBP is found in many carcinoma cells. eck expression was tested for by several methods, including immunoblotting of whole cell lysates and immunoprecipitation with anti-eck antibody from cell lysates. (Lindberg et al., supra) The results in Table 2 show that eck is expressed in many cell lines of epithelial origin, and in addition, is found in fibroblasts and melanoma cell lines.

TABLE 2

| Cell lines that express EBP: | |
| --- | --- |
| Cell line | Cell type |
| CaCo2 | Colon adenocarcinoma |
| FADU | Squamous carcinoma |
| T47D | Breast carcinoma |
| MDAMD361 | Breast adenocarcinoma |
| THP-1 | Monocytic leukemia |
| SKBR3 | Breast adenocarcinoma |
| CaOV4 | adenocarcinoma |
| MDAMB453 | Breast adenocarcinoma |
| Cakil | Kidney carcinoma |
| HBL100 | Breast |
| HT29 | Colon adenocarcinoma |
| JEG1 | Choriocarcinoma |
| 293 | Embryonic kidney |
| A704 | Kidney adenocarcinoma |
| Caki2 | Kidney adenocarcinoma |
| CaOV3 | Ovarian adenocarcinoma |
| SKOV3 | Ovarian adenocarcinoma |
| A172 | Glioblastoma |
| A431 | Epidermal carcinoma |
| BSC1 | Kidney |
| BT20 | Breast carcinoma |
| PC3 | Prostate adenocarcinoma |
| JAR | Choriocarcinoma |
| A498 | Kidney carcinoma |
| LNCaP | Prostate adenocarcinoma |
| BT474 | Breast carcinoma |
| SW480 | Colon adenocarcinoma |

TABLE 2-continued

Cell lines that express EBP:

| Cell line | Cell type |
|---|---|
| SW620 | Colon adenocarcinoma |
| MCF7 | Breast adenocarcinoma |
| T24 | Bladder carcinoma |
| 5637 | Bladder carcinoma |
| Du145 | Prostate carcinoma |
| SKNSH | Neuroblastoma |
| L929 | Connective tissue |
| G401 | Kidney Tumor |
| THP-1 | Monocytic leukemia |
| CCD11Lu | Lung |
| HT29 | Colon adenocarcinoma |
| SKOV3 | Ovarianadenocarcinoma |
| A172 | Glioblastoma |
| A431 | Epidermal carcinoma |
| JAR | Choriocarcinoma |
| GM4312A | Fibroblast |
| Wi38 | Lung |
| UT7 | Premegakaryocyte |
| CHOK1 | Ovary |
| HS249T | Melanoma |
| M14 | Melanoma |
| NIH3T3 | Fibroblast |

EXAMPLE 9

Biological Activities of EBP

A. Activity of EBP in Rat Wound Chamber Assay

The effects of recombinant CHO-derived and *E. coli* derived EBP on granulation tissue formation in subcutaneously implanted wound chambers in rats was studied.

Male Sprague-Dawley specific pathogen free rats (300–350 g; Charles River Breeding Laboratories, Inc.) were used for this study. Rats were anesthetized with sodium pentobarbital (50 mg/kg body weight) by intraperitoneal injection. Using aseptic surgical technique, a 3 cm midline incision was made on the dorsal surface of the rat. A single pocket was formed under the panniculus carnosis by blunt dissection on one side of the animal. A 3 cm long×1 cm diameter sterile stainless steel wire mesh cylinder was then inserted subcutaneously. The wound chambers used were similar to those described by Schilling et. al. (*Surgery* 46, 702–710 (1959)) and utilized by Hunt et. al. (*Am. J. Surg.* 114, 302–307 (1967)) as wound healing models. The incision was closed with wound clips. The rats survived the operation well with no evidence of postoperative discomfort. Beginning 3 days after wound chamber implantation, the rats were randomly divided into 5 groups. At this time daily injections of 1) 10 $\mu$g CHO-derived EBP, 2) 1 $\mu$g CHO-derived EBP, 3) 8 $\mu$g *E.coli*-derived EBP, 4) 5 $\mu$g recombinant platelet derived growth factor (PDGF), or 5) 0.1 ml sterile PBS and 1 mM CHAPS were begun and continued for a total of 9 days. The injections were made directly into the wound chamber through a silicone septum at the outer edge of the chamber. Twelve days after chamber implantation, the rats were sacrificed by $CO_2$ asphyxiation. Immediately after sacrifice, the chambers were removed surgically and carefully opened. The enclosed granulation tissue was then weighed, and stored at −70° C. for future processing.

Granulation tissue samples were thawed and homogenized with a Polytron homogenizer in 2 ml of ice-cold distilled water for approximately 1 minute. Next, 2 ml of ice-cold 10% trichloroacetic acid was added to the homogenate and incubated at 4° C. for 1 hour. The TCA-precipitated samples were centrifuged (500 g, 10 minutes) at 4° C., washed once with 2 ml of ice-cold 5% TCA, and finally washed with 2 ml of ice-cold 95% ethanol containing 50 mM sodium acetate. Samples were defatted twice with 2 ml of ethanol:ether (3:1, v/v) at 20° C. After each defatting procedure, samples were centrifuged (500×g, 10 minutes) and the supernate discarded. The pellet was then dissolved in 1N sodium hydroxide and brought up to a volume of 10 ml.

Total protein was determined by taking an aliquot of the solubilized granulation tissue and assaying the sample according to the method of Bradford (Anal. Biochem. 72, 248–251 (1976)) Bovine serum albumin (Sigma Chemical Co., St. Louis, Mo.) was used for a protein standard curve.

Total DNA content was determined as deoxy-ribose by the calorimetric method of Burton (Biochem. J. 62, 315 (1956)). Briefly, a 1 ml aliquot of the solubilized sample (in N NaOH) was neutralized with the addition of 0.5 ml of 2 N HCl. A 1 ml aliquot of the neutralized solution was extracted in 10% perchloric acid at 90° C. for 15 minutes. A 1 ml portion of the final extract was added to 2 ml activated diphenylamine (Sigma Chemical, St. Louis, Mo.) reagent and absorbance at 600 nm was measured after overnight incubation at room temperature. Hydrolyzed calf thymus DNA (Sigma) was used to construct the standard curve. The DNA content was measured as a rough index of the number of cells in the wound chamber, with the realization that cell type and cell cycle status also influence DNA content.

Total glycosaminoglycans (GAGs) were determined using chondroitin sulfate as a standard. A spectrophotometric assay for GAGs was run utilizing a change in absorption spectrum of the dye 1,9-dimethyl methylene blue (Farndale et al. Conn. Tiss. Res. i, 247–248 (1982)).

Total collagen content was determined as hydroxyproline (an index of collagen content) after hydrolysis of the solubilized granulation tissue in 6N HCl at 110° C. for 24 hours. Aliquots of 200 $\mu$l sample hydrolyzate were dried down, reconstituted in 200 $\mu$l of buffer and analyzed for hydroxy-L-proline by amino acid analysis using a Beckman 6300 amino acid analyzer. Quantitation was done using an external standard of hydroxy-L-proline (Sigma).

The data was analyzed by one-way analysis of variance. Significant differences were then analyzed comparing individual group means using a two-tailed unpaired student's t test. Statistical significance was defined as $p<0.05$. All values are expressed as mean ± SEM.

CHO-derived rEBP at a dose of 10 $\mu$g per chamber per day for 9 consecutive days and rPDGF at a dose of 5 $\mu$g per day (×9 days) both significantly increased the wet weight, total protein, total DNA and total GAG content of the chamber granulation tissue as compared to vehicle-treated (PBS and 1 mM CHAPS) control rats (see Table 3). All chambers were harvested 12 days after implantation. This timepoint is at the peak of granulation tissue formation and at the early stages of collagen formation. CHO-derived rEBP at a dose of 1 $\mu$g per chamber per day showed a significant increase in granulation tissue wet weight and GAG content over vehicle treated control rat chambers. However, there were no significant differences against control in the total protein, DNA, and hydroxyproline content for the 1 $\mu$g rEBP dose.

The accumulation of collagen is probably the single most important factor contributing to wound strength. PDGF treated chambers showed an 82% increase in hydroxyproline content (and therefore collagen synthesis) over control chambers. CHO-derived rEBP showed a 21% increase in hydroxyproline at 1 $\mu$g/chamber/day, and a 35% increase in hydroxyproline at 10 $\mu$g/chamber/day, although these increases were not statistically significant.

TABLE 3

Effects of CHO-Derived EBP on Granulation Tissue Formation in Wound Chambers in Rats

| TREATMENT | WET WEIGHT (mg) | TOTAL PROTEIN (mg) | DNA (µg) | HYDROXY-PROLINE (µg) | TOTAL GYLCOSAMINO-GLYCANS (µg) | CHANGE IN BODY WEIGHT (g) |
|---|---|---|---|---|---|---|
| Control | 158.6 ± 17.9 | 2.76 ± 0.27 | 153 ± 20 | 263.5 ± 29.1 | 383.3 ± 41.5 | +53.8 ± 5.4 |
| PDGF 5 ug | 417.4 ± 81.8** | 7.46 ± 1.52** | 356 ± 64** | 478.4 ± 85.9* | 725.2 ± 104.4** | +45.4 ± 2.8 |
| CHO-EBP 10 µg | 398.2 ± 70.9** | 7.15 ± 1.23** | 650 ± 163* | 354.5 ± 63.7 | 627.9 ± 92.4* | +50.3 ± 5.2 |
| CHO-EBP 1 µg | 238.0 ± 24.1* | 3.88 ± 0.44 | 232 ± 41 | 318.7 ± 31.7 | 589.2 ± 68.4* | +48.5 ± 4.9 |

Figure 8:
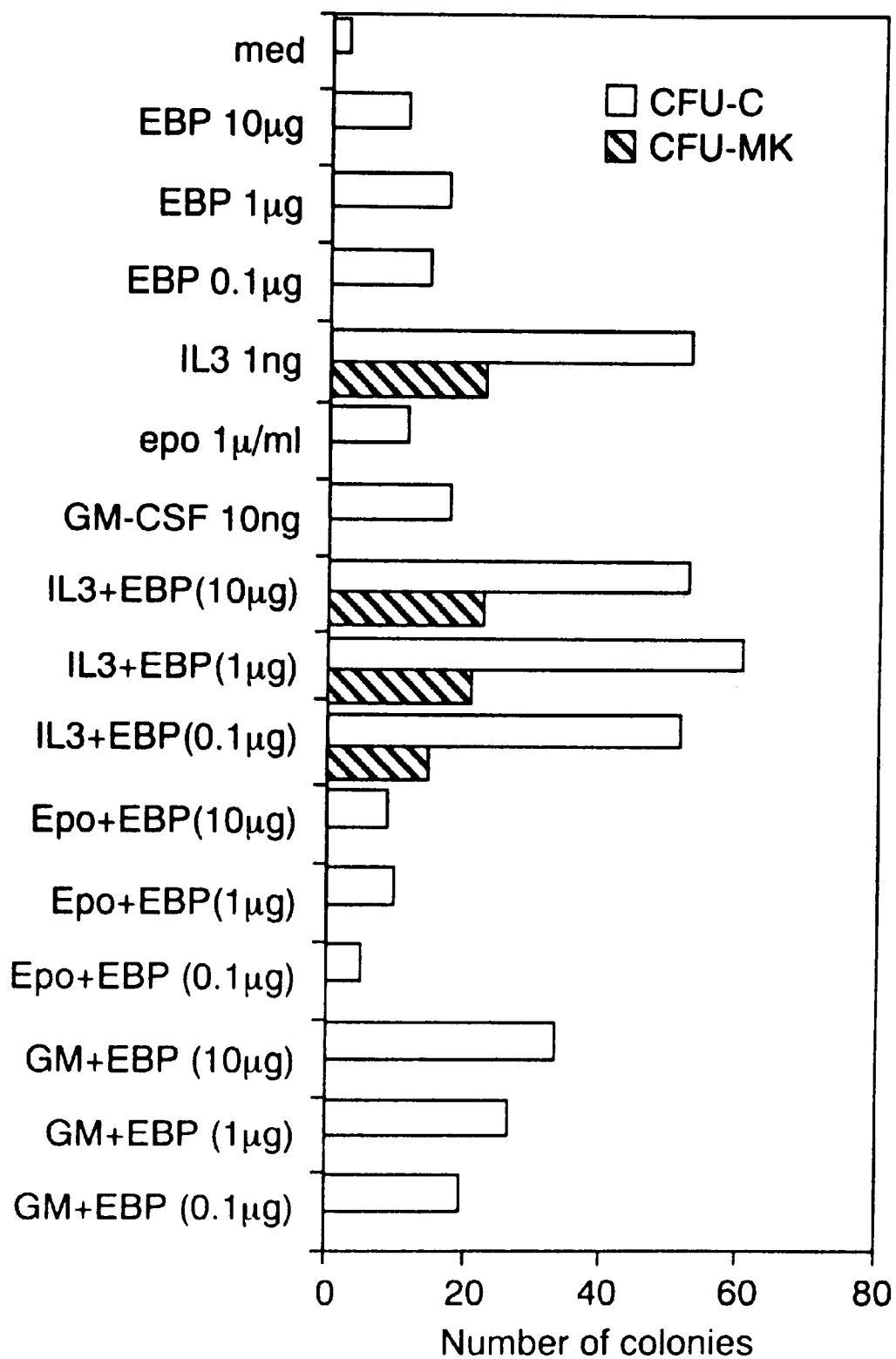
FIG. 8. CFU-C and CFU-Mk formation in bone marrow cultures in the presence of EBP alone and in combination with IL-3, erythropoietin or GM-CSF.

All Values are Mean ± SEM
*p < 0.05 by two-tailed unpaired Student's t test vs. control group
*p < 0.01 by two-tailed unpaired Student's t test vs. control group B. Activity of EBP in Murine Hematopoiesis Unfractionated bone marrow suspensions from BDF mice were plated into serum free culture medium (Iscove's modified Dulbecco's medium) in 0.3% agarose and incubated at 37° C., 5% $CO_2$ for ten days at a cell concentration of $1 \times 10^5$/ml in 96 well plates. Total volume per cell was 50 µl. EBP and other growth factors were added in the amounts indicated and colonies were scored at the tenth day of incubation. The results are shown in FIG. 8.

EBP at 1 µg/ml could potentiate murine IL-3 dependent murine CFU-C formation about 2-fold compared to IL-3 alone. CFU-C represents CFU-G, CFU-GM and CFU-M. EBP alone showed no stimulation of CFU-M or BFU-E/CFU-E.

C. Activity of EBP in Colon Crypt Assay

Colons from five (BDF) mice were removed and crypts isolated using a non enzymatic (EDTA) extraction method. Briefly, colons are washed and allowed to sit for 20 min. in a solution of PBS containing 0.04% sodium hypochlorite. Crypts are isolated by incubating the tissue for 1 hour at 37° C. in a solution of PBS containing 3 mM EDTA and 0.5 mM DTT. Crypts are then subjected to pancreatin digestion (0.2% in PBS) for 90 min. at 37° C. in order to obtain a single cell suspensing. Cells are washed in PBS, counted and viability determined by trypan blue exclusion (85% in this experiment). Cells are then plated in a top layer of 0.37% Sigma low melt agar onto a bottom layer of 0.5% agar. The RPMI media used in the agar includes the presence of 1× ITS (insulin, transferrin, and selenium, Gibco). Incubations were done in the presence of 1% fetal calf serum (FCS) and the indicated growth factors at the following concentration: TGFα, 50 ng/ml; bFGF, 60 ng/ml; EBP, 500 ng/ml. Control incubations lacked growth factors and/or FCS. Each of the various culture conditions was performed in triplicate and scored every several days.

Positive results were obtained after crypt cells were incubated with 1% FCS and EBP or 1% FCS and bFGF. In both conditions, the clusters of cells were large and the individual cells within the clusters appear healthy. In some cases the clusters were crypt-like shaped. When both EBP and bFGF were added together with FCS, fewer and smaller clusters appeared compared to when either growth factor was added alone in the presence of 1% FCS. Initially, the combination of EBP and bFGF appeared to be inducing cell growth but this stimulation in growth was short lived. In the plates with EBP alone (no serum) there were occasional large clusters, however these were looser, the cells were larger and roughly half the cells were nonviable within the cluster.

These results suggest that EBP is involved in the proliferation, differentiation or reformation of colon crypt cells.

TABLE 4

Activity of EBP in Colon Crypt Assay

| DAYS | TGFα | TGFα + EBP | EBP | bFGF | EBP + bFGF | 1% FCS + EBP | 1% FCS + bFGF | 1% FCS + EBP + bFGF | 1% FCS | NT |
|---|---|---|---|---|---|---|---|---|---|---|
| 2 | -- | -- | -- | -- | +++ | ++ | ++1/2+ | ++ | -- | -- |
| 5 | -- | -- | -- | -- | ++ | +++ | ++++ | +++ | + | -- |
| 7 | -- | -- | +/-- | -- | +/-- | ++++ | ++ | ++ | -- | -- |
| 9 | -- | -- | +/-- | -- | -- | +++ | ++++ | ++ | -- | -- |
| 12 | -- | -- | +/-- | -- | +/-- | +++ | ++++ | ++ | -- | -- |

NT—not tested

D. Activity of EBP on Primary Cultures of Hepatocytes

Hepatocytes were isolated by the in situ two step collagenase perfusion technique described by Seglen (Methods in Toxicol., Vol. 1A, 231–243 (1993). Briefly, the perfused livers were dispersed in ice cold Hank's buffer, filtered through a nylon mesh, and hepatocytes separated from nonparenchymal cells by repeated centrifugation at 50×g. The hepatocytes were determined to be greater than 85% viable by trypan blue exclusion. The hepatocytes were cultured on plates coated with rat tail collagen and plated in Williams E containing 5% FCS, $10^7$ M insulin, $10^8$ M dexamethason, glutamine, penicillin and streptomycin.

Figure 9:
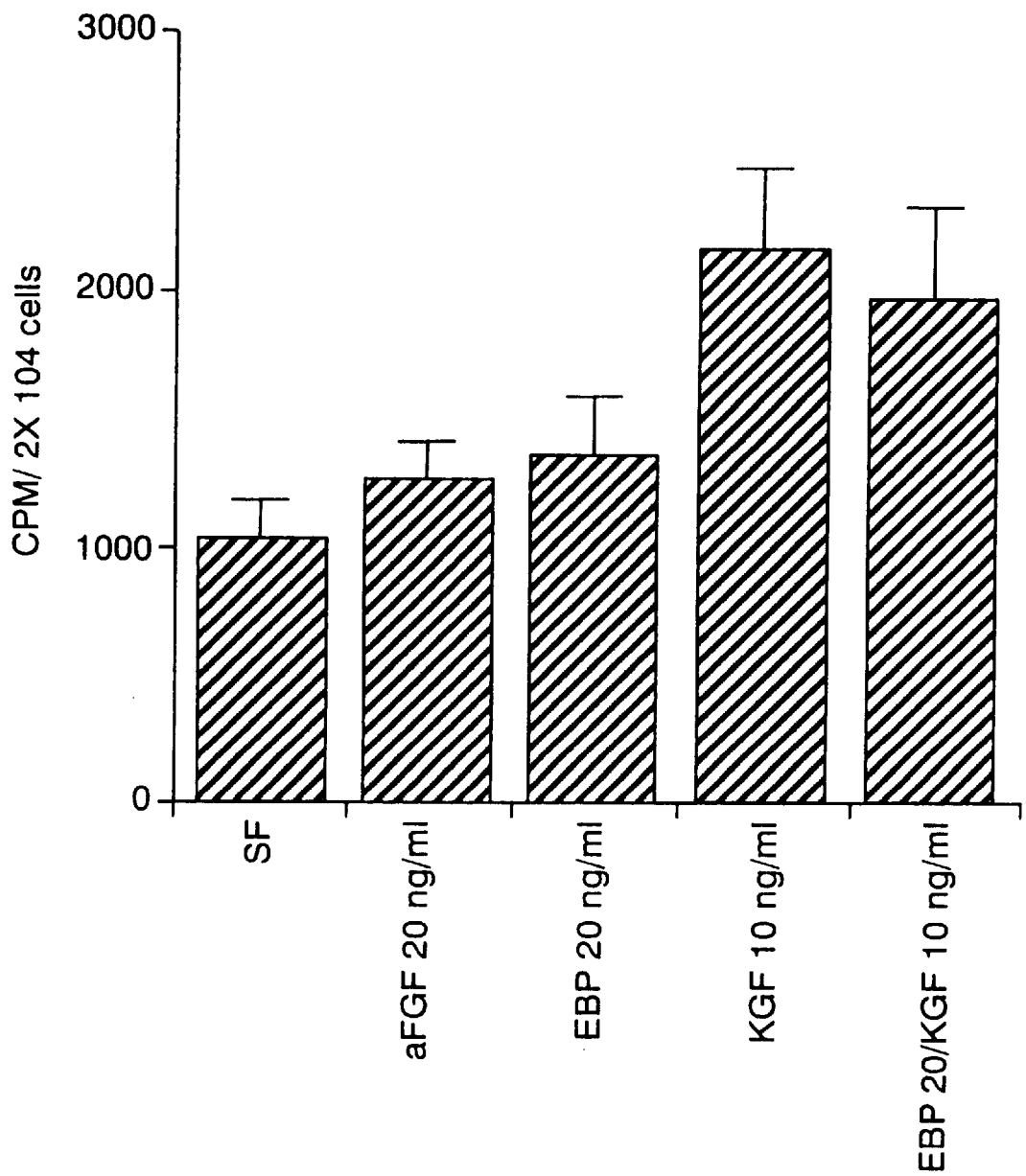
FIG. 9. Incorporation of $^3$H-thymidine in hepatocyte cultures in the presence of EBP, acidic FGF or KGF.

Cells were allowed to attach for 3-4 hours in serum containing media and then transferred to serum-free media. The appropriate concentrations of EBP or other growth factors were added and the cells were incubated for 24 to 48 hours in the presence of $^3$H-thymidine. After incubation, the extent of $^3$H-thymidine incorporation into cells was determined. The growth factors tested were keratinocyte growth factor (KGF) at 10 ng/ml, acidic FGF (aFGF) at 20 ng/ml, and EBP at 20 ng/ml. The results are shown in FIG. 9. The amount of $^3$H-thymidine incorporation stimulated by EBP is about the same as that induced by aFGF. The combination of KGF and EBP did not stimulate hepatocyte growth over the level observed by KGF alone. In this particular experiment, the serum free value was unusually high (about 3-fold).

EXAMPLE 10

Neurotrophic Activity of EBP

A. Promotion of neuronal survival and neurite outgrowth in embryonic rat spinal cord neurons Recombinant soluble EBP was produced in CHO cells and purified as described in Example 4. Monolayer cultures of dissociated cells were prepared from spinal cords of 15-16 day-old Sprague-Dawley rat embryos as previously described (Magal et al., Dev. Brain Res. 63, 14–150 (1991)). Briefly, a single cell suspension was prepared from spinal cords and seeded at about 25,000 cells in 90 μl per well in 96-well plates, sequentially precoated with polyornithine (Sigma; 0.1 mg/ml) and laminin (Gibco; 1 mg/ml). The culture medium was Leibovitz L-15 medium, 5% heat-inactivated horse serum, 0.5% heat-inactivated fetal calf serum, sodium bicarbonate (2.5 g/L), D-glucose (9 g/L), L-glutamine (2 mM), penicillin (100 mg/ml) and a mixture of amino acids and vitamins. Different concentrations of EBP were added to the cells at the time of seeding, in a volume of 10 μl per well, completing the volume to 100μl/well. Media and treatments were renewed every other day. Control cultures received 10 μl of medium without EBP. At designated time periods, cultures were fixed with 4% paraformaldehyde for 30 min at room temperature, washed with PBS, permeabilized with 1% Triton X-100 and blocked for 30 min at room temperature with 5% normal horse serum in PBS containing 0.1% Triton X-100. Anti-MAP2 mouse monoclonal IgG (Boehringer Mannheim), at 1:1000 dilution, was applied in the blocking solution overnight at 4° C. Subsequently cultures were incubated in biotinylated mouse IgG, at a 300-fold dilution for 1.5h at room temperature. Next, the cultures were incubated for 45 min. at room temperature in avidin-biotin-peroxidase complex in PBS containing 0.1% triton X-100, washed again with PBS and reacted for 5 min. in 0.1M Tris-HCl containing 0.04% 3',3'-diaminobenzidine tetrachloride, 0.06% $NiCl_2$ and 0.02% $H_2O_2$. The effect of EBP on the survival of spinal cord neurons was quantified by counting all the MAP2 positive cells in the well.

Figure 10:
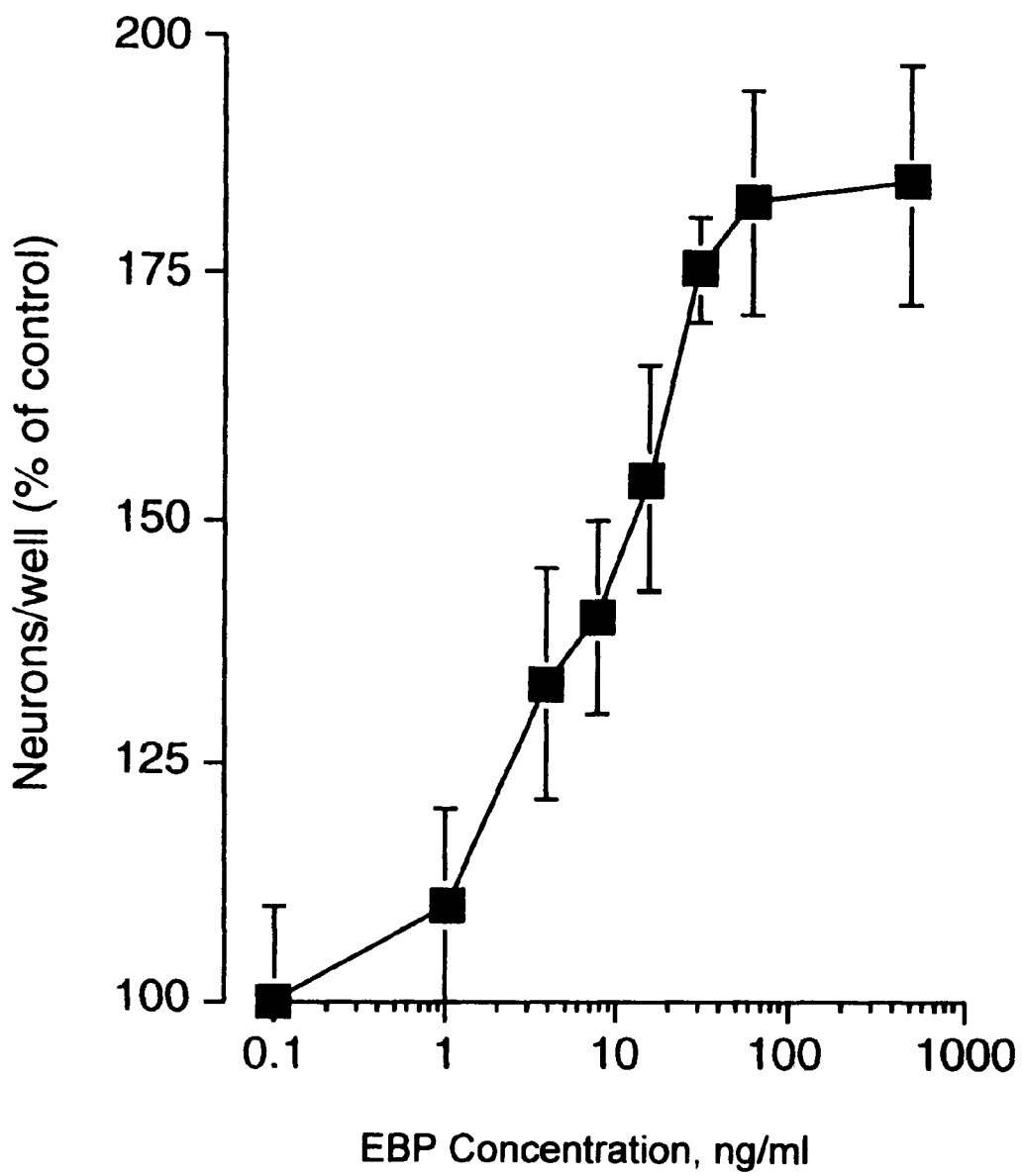
FIG. 10. EBP promotes neuronal survival in cultured spinal cord neurons. Concentration-dependence of EBP effect on the number of spinal cord neurons in 9-day old cultures is shown, expressed as percent of control level at that time. Each value is mean ± standard deviation of 3-4 independent cultures. Differences between controls and treated cultures are highly significant (P<0.005; t test).

FIG. 10 shows that EBP increased neuronal survival after 9 days in culture in a dose-dependent manner. Survival was enhanced by as much as 84% with an $ED_{50}$ of less than 10 μg/ml. In addition, neurites in EBP-treated cultures were longer and more elaborated compared to control cultures (FIG. 11a through f).

B. Involvement of Eck receptor in EBP-mediated neurotrophic activity.

Partially purified spinal cord motor neuron cultures (approximately 70%–75% motor neurons) were prepared as previously described (Camu and Henderson, J. Neurosci. Methods 44, 59–70 (1992)) with slight modifications. Briefly, ventral spinal cords were dissected from 15 day old Sprague-Dawley rat embryos and incubated in 0.05% trypsin in PBS for 17 minutes at 37° C., after which a 10% volume of fetal calf serum was added. Subsequently cells were resuspended in dissociation media composed of L15 medium without sodium bicarbonate (Gibco) supplemented with 5 μg/ml insulin, 0.1 mM putrescine, 0.1 mg/ml conalbumin, 30 nM sodium selenite, 20 nM progesterone, 20 mM glucose, 100 IU/ml penicillin, 100 μg/ml streptomycin, 0.1% BSA and 250 Units/ml of DNase. The tissue was dissociated by gentle trituration through a Gilson blue piptette tip until a single cell suspension was obtained. The resulting suspension was filtered through 40 μm nylon mesh and applied on top 4 ml of 6.8% metrizamide in 15 ml polystryrene tubes. The tubes were centrifuged for 20 minutes at 1650 rpm in a bench-top Beckman centrifuge. Large cells, which formed a sharp band on the top of the metrizamide cushion, were washed in 4 volumes of the dissociation media and layered onto 2 ml of 4% BSA. The cells were centrifuged for 10 min at 800 rpm. The resulting cell pellet was resuspended in culture medium (DMEM/F12 and B27 (Gibco) supplemented with 10% fetal bovine serum), and subsequently plated in Terasaki wells (HLA plates, Nunc) pre-coated with poly-ornithine and laminin), at a density of 6,000–10,000 cells/well in 90 μl of medium. The treatments, which included the addition of EBP, EBP and anti-Eck antibodies, and finally EBP and anti-EBP antibodies, were added at 10× concentration in 10 μl/well. The anti-Eck monoclonal antibodies were obtained by using recombinant human Eck extracellular domain (ECK-X) prepared as described in Example 1, as the antigen. The antibodies were purified from ascites using protein A-sepharose. Anti-ECK1 and anti-ECK2 antibodies recognize different epitopes in human Eck. The anti-ECK1 antibody recognizes human and rat Eck while anti-ECK2 antibody recognizes only human Eck. After 3 days, the cultures were fixed in 2% paraformaldehyde for 15 minutes at room temperature. Phase-bright cells with neuronal morphology and without vacuolar inclusions were counted in 2 crossing strips per well at 100× magnification, representing 20% of the well's surface area. Neurite length was measured from photographs as the distance between the cell soma and the tip of the longest neurite, using the Jandel Video Analysis Software (JAVA).

FIG. 12 shows that EBP acts through the Eck receptor to enhance neural survival and neurite outgrowth in cultures enriched for motor neurons. EBP activity is abolished in the presence of the anti-ECK1 antibody or the anti-EBP antibody, but is not affected by addition of the anti-ECK2 antibody.

C. Effects of EBP on other neuron types.

Experiments similar to those described in Part A were performed on neural cultures derived from rat embryonic midbrain and mesencephalon (TH-positive dopaminergic neurons), hippocampus (pyramidal neurons) and postnatal locus coeroleus (TH-positive noradrenergic neurons). Preparation of rat day 16 midbrain cultures, rat day 20 mesencephalon cultures, rat day 20 hippocampus cultures and postnatal rat 4-5 day locus coeroleus cultures was essentially as described in Magal et al. Neuroscience 52, 867–881 (1993), Magal et al. Neuro Report 4, 779–782 (1993), and Louis et al. Eur. J. Neurosci.5, 1610–1621 (1993). The results presented in Table 5 show that EBP mediates survival of neurons in all four cultures tested, proving that EBP can promote the survival of dopaminergic, pyramidal and noradrenergic neurons.

TABLE 5

| Neuronal Culture | Neuron Type | # of neurons/well (mean ± S.E.) | | |
|---|---|---|---|---|
| | | −EBP | +EBP | |
| E16 midbrain | dopaminergic/TH-positive | 36.7 ± 4.64 (5 days)[a] | 62.3 ± 2.62 | (20 ng/ml)[b] |
| E20 mesencephalon | dopaminergic/TH-positive | 40.3 ± 1.25 (3 days) | 71.5 ± 8.40 | (1000 ng/ml) |
| | | | 87.0 ± 8.98 | (3500 ng/ml) |
| | | | 57.7 ± 1.25 | (250 ng/ml) |
| E20 hippocampal | gabaergic/GABA-positive | 948.5 ± 65.5 (3 days) | 1306.5 ± 88.5 | (200 ng/ml) |
| | | | 972.0 ± 14.0 | (50 ng/ml) |
| P5 locus coeroleus | norademergic/TH-positive | 54.0 ± 6.40 (4 days) | 81.0 ± 10.12 | (500 ng/ml) |

[a]Number of days in culture ± EBP
[b]Final concentration of EBP added to culture While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method for promoting neuron survival or neurite outgrowth comprising contacting neurons with an amount of an eck receptor binding protein comprising the amino acid sequence shown in SEQ ID NO:1 or a fragment thereof effective in promoting neuron survival or neurite outgrowth.

2. The method according to claim 1 further comprising administering a therapeutically effective amount of a ciliary neurotrophic factor, brain derived neurotrophic factor, glial derived neurotrophic factor, nerve growth factor, insulin-like growth factor-1 or neurotrophin-3.

3. The method according to claim 1 wherein the neurons are dopaminergic, pyramidal, noradrenergic or motor neurons.

4. A method for culturing neurons for transplantation comprising adding an amount of an eck receptor binding protein effective in promoting neuron survival or to cell culture media comprising the neurons, wherein the eck receptor binding protein comprises the amino acid sequence as shown in SEQ ID NO:1 or a fragment thereof effective in promoting neuron survival.

5. The method according to claim 4 wherein the neurons are fetal neurons.

6. The method according to claim 4 further comprising adding an effective amount of a ciliary neurotrophic factor, brain derived neurotrophic factor, glial derived neurotrophic factor, nerve growth factor, insulin-like growth factor-1 or neurotrophin-3.

7. The method of claim 4 wherein the neurons are dopaminergic, pyramidal, noradrenergic or motor neurons.

* * * * *

UNITED STATES PATENT AND TRADEMARK OFFICE
CERTIFICATE OF CORRECTION

PATENT NO. : 6,087,167

DATED : July 11, 2000

INVENTOR(S) : Bartley et al.

It is certified that error appears in the above-identified patent and that said Letters Patent is hereby corrected as shown below:

Column 1, line 44: Change "Lev et al i" to -- Lev et al. ibid --
Column 6, line 23: Change "ind" to -- bind -- after "specifically"
Column 8, line 17: Change "suora" to -- supra --
Column 9, line 13: Change "semulating" to -- stimulating --
Column 12, line 50: Change "2 mM" to -- 25mM --
Column 14, line 30: Change "Mr" to -- $M_r$ --
Column 14, line 63: Change "2" to -- 230 -- after "science"
Column 15, line 17: Change "700° C" to -- 70° C --
Column 15, line 37: Change "mCR" to -- PCR --
Column 17, line 9: Change "$EFBP^{1-150}$" to -- $EBP^{1-150}$ --
Column 19, line 50: Change "10pM" to -- 10µM --
Column 19, line 66: Change "40°" to -- 4° --
Column 20, line 42: Change "$M\pm0.3\times10^{8}$" to -- $M\pm0.3\times10^{-8}$ --
Column 21, line 14: Change "Tris-Hcl HCl" to -- Tris-HCl --
Column 23, line 13: Insert the table header -- <u>Cell lines that express eck:</u> -- between "G401 Kidney Tumor" and "THP-1 Monocytic leukemia"
Column 24, line 14: Change "calorimetric" to -- colorimetric --
Column 24, line 31: Change "i" to -- 9 --
Column 25, line 15: Change "*p<0.01" to -- **p<0.01 --
Column 25, line 45: Change "NT - not tested" to -- NT - not treated --
Column 26, line 58: Change "$10^{8}$" to -- $10^{-8}$ --

UNITED STATES PATENT AND TRADEMARK OFFICE
CERTIFICATE OF CORRECTION

PATENT NO. : 6,087,167
DATED : Jul. 11, 2000
INVENTOR(S) : Bartley et al.

It is certified that error appears in the above-identified patent and that said Letters Patent is hereby corrected as shown below:

Column 40, line 51: Remove "or" after "survival"

Signed and Sealed this

Twenty-fourth Day of April, 2001

Attest:

NICHOLAS P. GODICI

Attesting Officer      Acting Director of the United States Patent and Trademark Office

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 205 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Glu Phe Leu Trp Ala Pro Leu Leu Gly Leu Cys Cys Ser Leu Ala
 1               5                  10                  15

Ala Ala Asp Arg His Thr Val Phe Trp Asn Ser Ser Asn Pro Lys Phe
                20                  25                  30

Arg Asn Glu Asp Tyr Thr Ile His Val Gln Leu Asn Asp Tyr Val Asp
            35                  40                  45

Ile Ile Cys Pro His Tyr Glu Asp His Ser Val Ala Asp Ala Ala Met
    50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
               100                 105                 110

Pro Phe Thr Leu Gly Lys Glu Phe Lys Glu Gly His Ser Tyr Tyr Tyr
           115                 120                 125

Ile Ser Lys Pro Ile His Gln His Glu Asp Arg Cys Leu Arg Leu Lys
   130                 135                 140

Val Thr Val Ser Gly Lys Ile Thr His Ser Pro Gln Ala His Val Asn
145                 150                 155                 160

Pro Gln Glu Lys Arg Leu Ala Ala Asp Asp Pro Glu Val Arg Val Leu
               165                 170                 175
```

```
His Ser Ile Gly His Ser Ala Ala Pro Arg Leu Phe Pro Leu Ala Trp
            180                 185                 190

Thr Val Leu Leu Leu Pro Leu Leu Leu Leu Gln Thr Pro
        195                 200                 205
```

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

AAGCATATGG ATCGCCACAC CGTCTTCTGG          30

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GAAGGATCCT TATCACGGGG TTTGCAGCAG CAGAA      35

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GAAGGATCCC TATTATGCTG CAAGTCTCTT CTCCTG     36

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GAATTCAAGC TTCAGGCCCC GCGCTATGGA G         31

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GAATTCTCTA GATCATCACG GGGTTTGCAG CAGCA                            35
```

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
AGCTTAGATC TCC                                                   13
```

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
AATTGGAGAT CTA                                                   13
```

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AATTCCAGAC GCTGTCCCCG GAGGGATCCG GCAACTGAG                       39
```

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
TCGACTCAGT TGCCGGATCC CTCCGGGGAC AGCGTCTGG                       39
```

(2) INFORMATION FOR SEQ ID NO:11:

(i) SEQUENCE CHARACTERISTICS:
        (A) LENGTH: 1480 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 74..689

(xi) SEQUENCE DESCRIPTION: SEQ ID NO:11:

```
GCGGAGAAAG CCAGTGGGAA CCCAGACCCA TAGGAGACCC GCGTCCCCGC TCGGCCTGGC        60

CAGGCCCCGC GCT ATG GAG TTC CTC TGG GCC CCT CTC TTG GGT CTG TGC         109
           Met Glu Phe Leu Trp Ala Pro Leu Leu Gly Leu Cys
             1           5                  10

TGC AGT CTG GCC GCT GCT GAT CGC CAC ACC GTC TTC TGG AAC AGT TCA         157
Cys Ser Leu Ala Ala Ala Asp Arg His Thr Val Phe Trp Asn Ser Ser
         15              20                  25

AAT CCC AAG TTC CGG AAT GAG GAC TAC ACC ATA CAT GTG CAG CTG AAT         205
Asn Pro Lys Phe Arg Asn Glu Asp Tyr Thr Ile His Val Gln Leu Asn
     30              35                  40

GAC TAC GTG GAC ATC ATC TGT CCG CAC TAT GAA GAT CAC TCT GTG GCA         253
Asp Tyr Val Asp Ile Ile Cys Pro His Tyr Glu Asp His Ser Val Ala
 45              50                  55                      60

GAC GCT GCC ATG GAG CAG TAC ATA CTG TAC CTG GTG GAG CAT GAG GAG         301
Asp Ala Ala Met Glu Gln Tyr Ile Leu Tyr Leu Val Glu His Glu Glu
             65                  70                  75

TAC CAG CTG TGC CAG CCC CAG TCC AAG GAC CAA GTC CGC TGG CAG TGC         349
Tyr Gln Leu Cys Gln Pro Gln Ser Lys Asp Gln Val Arg Trp Gln Cys
             80                  85                  90

AAC CGG CCC AGT GCC AAG CAT GGC CCG GAG AAG CTG TCT GAG AAG TTC         397
Asn Arg Pro Ser Ala Lys His Gly Pro Glu Lys Leu Ser Glu Lys Phe
             95                 100                 105

CAG CGC TTC ACA CCT TTC ACC CTG GGC AAG GAG TTC AAA GAA GGA CAC         445
Gln Arg Phe Thr Pro Phe Thr Leu Gly Lys Glu Phe Lys Glu Gly His
     110                 115                 120

AGC TAC TAC TAC ATC TCC AAA CCC ATC CAC CAG CAT GAA GAC CGC TGC         493
Ser Tyr Tyr Tyr Ile Ser Lys Pro Ile His Gln His Glu Asp Arg Cys
125              130                 135                 140

TTG AGG TTG AAG GTG ACT GTC AGT GGC AAA ATC ACT CAC AGT CCT CAG         541
Leu Arg Leu Lys Val Thr Val Ser Gly Lys Ile Thr His Ser Pro Gln
                 145                 150                 155

GCC CAT GTC AAT CCA CAG GAG AAG AGA CTT GCA GCA GAT GAC CCA GAG         589
Ala His Val Asn Pro Gln Glu Lys Arg Leu Ala Ala Asp Asp Pro Glu
                 160                 165                 170

GTG CGG GTT CTA CAT AGC ATC GGT CAC AGT GCT GCC CCA CGC CTC TTC         637
Val Arg Val Leu His Ser Ile Gly His Ser Ala Ala Pro Arg Leu Phe
         175                 180                 185

CCA CTT GCC TGG ACT GTG CTG CTC CTT CCA CTT CTG CTG CTG CAA ACC         685
Pro Leu Ala Trp Thr Val Leu Leu Leu Pro Leu Leu Leu Leu Gln Thr
     190                 195                 200

CCG T GAAGGTGTAT GCCACACCTG GCCTTAAAGA GGGACAGGCT GAAGAGAGGG            739
Pro
205

ACAGGCACTC CAAACCTGTC TTGGGGCCAC TTTCAGAGCC CCCAGCCCTG GGAACCACTC       799

CCACCACAGG CATAAGCTAT CACCTAGCAG CCTCAAAACG GGTCAGTATT AAGGTTTTCA       859

ACCGGAAGGA GGCCAACCAG CCCGACAGTG CCATCCCCAC CTTCACCTCG GAGGGACGGA       919

GAAAGAAGTG GAGACAGTCC TTTCCCACCA TTCCTGCCTT TAAGCCAAAG AAACAAGCTG       979

TGCAGGCATG GTCCCTTAAG GCACAGTGGG AGCTGAGCTG GAAGGGGCCA CGTGGATGGG      1039

CAAAGCTTGT CAAAGATGCC CCCTCCAGGA GAGAGCCAGG ATGCCCAGAT GAACTGACTG      1099

AAGGAAAAGC AAGAAACAGT TTCTTGCTTG GAAGCCAGGT ACAGGAGAGG CAGCATGCTT      1159

GGGCTGACCC AGCATCTCCC AGCAAGACCT CATCTGTGGA GCTGCCACAG AGAAGTTTGT      1219

AGCCAGGTAC TGCATTCTCT CCCATCCTGG GGCAGCACTC CCCAGAGCTG TGCCAGCAGG      1279

GGGGCTGTGC CAACCTGTTC TTAGAGTGTA GCTGTAAGGG CAGTGCCCAT GTGTACATTC      1339

TGCCTAGAGT GTAGCCTAAA GGGCAGGGCC CACGTGTATA GTATCTGTAT ATAAGTTGCT      1399
```

```
GTGTGTCTGT CCTGATTTCT ACAACTGGAG TTTTTTTATA CAATGTTCTT TGTCTCAAAA      1459

TAAAGCAATG TGTTTTTTCG G                                                1480
```

(2) INFORMATION FOR SEQ ID NO:12:

(i) SEQUENCE CHARACTERISTICS:
        (A) LENGTH: 205 amino acids
        (B) TYPE: amino acid
        (D) TOPOLOGY: linear (ii) MOLECULE TYPE: protein (xi) SEQUENCE DESCRIPTION: SEQ ID NO:12:

```
Met Glu Phe Leu Trp Ala Pro Leu Leu Gly Leu Cys Cys Ser Leu Ala
 1               5                  10                  15

Ala Ala Asp Arg His Thr Val Phe Trp Asn Ser Ser Asn Pro Lys Phe
             20                  25                  30

Arg Asn Glu Asp Tyr Thr Ile His Val Gln Leu Asn Asp Tyr Val Asp
         35                  40                  45

Ile Ile Cys Pro His Tyr Glu Asp His Ser Val Ala Asp Ala Ala Met
     50                  55                  60

Glu Gln Tyr Ile Leu Tyr Leu Val Glu His Glu Glu Tyr Gln Leu Cys
 65                  70                  75                  80

Gln Pro Gln Ser Lys Asp Gln Val Arg Trp Gln Cys Asn Arg Pro Ser
                 85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
    130                 135                 140

Val Thr Val Ser Gly Lys Ile Thr His Ser Pro Gln Ala His Val Asn
145                 150                 155                 160

Pro Gln Glu Lys Arg Leu Ala Ala Asp Asp Pro Glu Val Arg Val Leu
                165                 170                 175

His Ser Ile Gly His Ser Ala Ala Pro Arg Leu Phe Pro Leu Ala Trp
            180                 185                 190

Thr Val Leu Leu Leu Pro Leu Leu Leu Gln Thr Pro
        195                 200                 205
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Lys Arg Leu Ala Ala
 1               5
```

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS: single -continued (D) TOPOLOGY: linear (ii) MOLECULE TYPE: protein (xi) SEQUENCE DESCRIPTION: SEQ ID NO:14:

Asp Arg His Thr Val Phe Asp Asn Ser Ser Asn Pro Lys Phe Arg Asn
1               5                  10                  15

Glu Asp Tyr Ile His Val Gln
            20

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GAATTCTCTA GATTTCATGG AAGGAGCAGC ACAGTCCAG                          39

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GAATTCTCTA GATTATCATG GGAAGAGGCG TGGGGCAGC                          39

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GAATTCTCTA GATTATCATG GGGCAGCACT GTGACCGATG C                       41